(12) United States Patent
Zdeblick et al.

(10) Patent No.: US 7,300,440 B2
(45) Date of Patent: *Nov. 27, 2007

(54) METHODS AND INSTRUMENTS FOR INTERBODY FUSION

(75) Inventors: Thomas Zdeblick, Madison, WI (US); Lawrence M. Boyd, Memphis, TN (US); Eddie Ray, III, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/442,822

(22) Filed: May 21, 2003

(65) Prior Publication Data

US 2003/0195519 A1 Oct. 16, 2003

Related U.S. Application Data

(63) Continuation of application No. 09/746,300, filed on Dec. 21, 2000, now Pat. No. 6,595,995, which is a continuation of application No. 09/265,179, filed on Mar. 9, 1999, now Pat. No. 6,245,072, which is a continuation of application No. 09/176,972, filed on Oct. 22, 1998, now abandoned, which is a continuation of application No. 08/604,874, filed on Feb. 22, 1996, now abandoned, which is a continuation-in-part of application No. 08/411,017, filed on Mar. 27, 1995, now Pat. No. 5,782,919.

(51) Int. Cl.
  *A61B 17/32* (2006.01)

(52) U.S. Cl. ...................................................... 606/80

(58) Field of Classification Search ................ 600/204, 600/210, 214, 235, 154, 159; 606/80, 86, 606/90, 99, 96
See application file for complete search history.

(56) References Cited

U.S. PATENT DOCUMENTS 1,627,941 A    5/1927   Wappler (Continued)

FOREIGN PATENT DOCUMENTS

DE         3023942 A1    1/1982

(Continued)

OTHER PUBLICATIONS

*Posterior Lumbar Interbody Fusion Made Simple*, Neurological Surgery Associates of Cincinnati, Inc., Mar. 9, 1999.

(Continued)

*Primary Examiner*—Eduardo C. Robert
*Assistant Examiner*—Michael J. Araj
(74) *Attorney, Agent, or Firm*—Krieg DeVault LLP

(57) ABSTRACT

A laparoscopic surgical technique is provided for preparing a site for implantation of a fusion device or implant. In accordance with one embodiment of the technique, a laparoscope is provided having an outer sleeve with distraction fingers at one end to distract the disc space. The laparoscope includes a laparoscopic port at its opposite end through which instruments and implants are inserted. The laparoscope provides a sealed working channel to the disc space, through which the disc space is distracted, the vertebral endplates and surrounding disc is reamed, and the fusion device inserted. The laparoscope is alternately engaged within bilateral locations in the disc space for insertion of a pair of fusion implants. A switching sleeve extends through the laparoscope to protect the tissue at the surgical site as the laparoscope is moved between the bilateral fusion locations.

18 Claims, 14 Drawing Sheets

U.S. PATENT DOCUMENTS

| | | |
|---|---|---|
| 2,549,731 A | 4/1951 | Wattley |
| 3,486,505 A | 12/1969 | Morrison |
| 3,822,697 A | 7/1974 | Komiya |
| 3,844,291 A | 10/1974 | Moen |
| 3,848,601 A | 11/1974 | Ma et al. |
| 3,867,932 A | 2/1975 | Huene |
| 3,916,907 A | 11/1975 | Peterson |
| 4,059,115 A | 11/1977 | Jumashev et al. |
| 4,328,593 A | 5/1982 | Sutter et al. |
| 4,349,921 A | 9/1982 | Kuntz |
| 4,501,269 A | 2/1985 | Bagby |
| 4,545,374 A | 10/1985 | Jacobson |
| 4,557,255 A | 12/1985 | Goodman |
| 4,573,448 A | 3/1986 | Kambin |
| RE32,158 E | 5/1986 | Vukovic |
| 4,592,347 A | 6/1986 | Mahruki |
| 4,677,972 A | 7/1987 | Tornier |
| 4,714,469 A | 12/1987 | Kenna |
| 4,736,738 A | 4/1988 | Lipovsek et al. |
| 4,743,256 A | 5/1988 | Brantigan |
| 4,753,235 A | 6/1988 | Hasson |
| 4,834,757 A | 5/1989 | Brantigan |
| 4,877,020 A | 10/1989 | Vich |
| 4,878,915 A | 11/1989 | Brantigan |
| 4,936,848 A | 6/1990 | Bagby |
| 4,936,851 A | 6/1990 | Fox et al. |
| 4,961,740 A | 10/1990 | Ray et al. |
| 4,978,350 A | 12/1990 | Wagenknecht |
| 4,997,432 A | 3/1991 | Keller |
| 5,015,247 A | 5/1991 | Michelson |
| 5,015,255 A | 5/1991 | Kuslich |
| 5,026,373 A | 6/1991 | Ray et al. |
| 5,055,104 A | 10/1991 | Ray |
| 5,062,845 A | 11/1991 | Kuslich et al. |
| 5,113,846 A * | 5/1992 | Hiltebrandt et al. ........ 600/225 |
| D331,625 S | 12/1992 | Price |
| 5,178,133 A * | 1/1993 | Pena ........................ 600/203 |
| 5,192,327 A | 3/1993 | Brantigan |
| 5,195,541 A | 3/1993 | Obenchain |
| 5,222,973 A | 6/1993 | Sharpe et al. |
| 5,263,953 A | 11/1993 | Bagby |
| 5,306,309 A | 4/1994 | Wagner et al. |
| 5,309,896 A * | 5/1994 | Moll et al. .................. 600/207 |
| 5,313,962 A | 5/1994 | Obenchain |
| 5,352,231 A | 10/1994 | Brumfield et al. |
| 5,354,302 A | 10/1994 | Ko |
| 5,357,983 A | 10/1994 | Mathews |
| 5,358,511 A | 10/1994 | Gatturna et al. |
| 5,395,317 A | 3/1995 | Kambin |
| 5,397,364 A | 3/1995 | Kozak et al. |
| 5,400,805 A | 3/1995 | Warren |
| 5,423,825 A | 6/1995 | Levine |
| 5,423,855 A | 6/1995 | Marienne |
| 5,425,772 A | 6/1995 | Brantigan |
| 5,431,658 A | 7/1995 | Moskovich |
| 5,439,464 A | 8/1995 | Shapiro |
| 5,443,514 A | 8/1995 | Steffee |
| 5,454,811 A | 10/1995 | Huebner |
| 5,458,638 A | 10/1995 | Kuslich et al. |
| 5,470,334 A | 11/1995 | Ross et al. |
| 5,480,403 A | 1/1996 | Lee et al. |
| 5,484,437 A | 1/1996 | Michelson |
| 5,489,307 A | 2/1996 | Kuslich et al. |
| 5,489,308 A | 2/1996 | Kuslich et al. |
| 5,499,997 A | 3/1996 | Sharpe et al. |
| 5,505,732 A | 4/1996 | Michelson |
| 5,514,148 A | 5/1996 | Smith, III |
| 5,522,899 A | 6/1996 | Michelson |
| 5,534,031 A | 7/1996 | Matsuzaki et al. |
| 5,540,711 A * | 7/1996 | Kieturakis et al. .......... 606/192 |
| 5,549,679 A | 8/1996 | Kuslich |
| 5,554,191 A | 9/1996 | Lahille et al. |
| D374,283 S | 10/1996 | Michelson |
| 5,562,736 A | 10/1996 | Ray et al. |
| 5,571,109 A | 11/1996 | Bertagnoli |
| 5,571,189 A | 11/1996 | Kuslich |
| 5,571,192 A | 11/1996 | Schönhöffer |
| D377,096 S | 12/1996 | Michelson et al. |
| 5,584,847 A * | 12/1996 | Duluco et al. ............... 606/185 |
| 5,591,207 A | 1/1997 | Coleman |
| 5,591,235 A | 1/1997 | Kuslich |
| 5,593,409 A | 1/1997 | Michelson |
| 5,599,279 A | 2/1997 | Slotman et al. |
| 5,603,702 A | 2/1997 | Smith et al. |
| 5,609,635 A | 3/1997 | Michelson |
| 5,609,636 A | 3/1997 | Kohrs et al. |
| 5,645,549 A | 7/1997 | Boyd et al. |
| 5,653,761 A | 8/1997 | Pisharodi |
| 5,653,762 A | 8/1997 | Pisharodi |
| 5,658,336 A | 8/1997 | Pisharodi |
| 5,669,909 A | 9/1997 | Zdeblick et al. |
| 5,700,291 A | 12/1997 | Kuslich et al. |
| 5,741,253 A | 4/1998 | Michelson |
| 5,755,732 A | 5/1998 | Green et al. |
| 5,772,661 A * | 6/1998 | Michelson ................... 606/61 |
| 5,782,830 A | 7/1998 | Farris |
| D397,436 S | 8/1998 | Michelson |
| 5,843,039 A * | 12/1998 | Klemm .................. 604/164.01 |
| 5,843,121 A | 12/1998 | Yoon |
| 5,860,973 A | 1/1999 | Michelson |
| 5,865,847 A | 2/1999 | Kohrs et al. |
| 5,885,299 A | 3/1999 | Winslow et al. |
| 5,888,224 A | 3/1999 | Beckers et al. |
| 5,893,890 A | 4/1999 | Pisharodi |
| 5,897,593 A | 4/1999 | Kohrs et al. |
| 5,906,616 A | 5/1999 | Pavlov et al. |
| 5,928,242 A | 7/1999 | Kuslich et al. |
| 5,968,098 A | 10/1999 | Winslow |
| 5,984,967 A | 11/1999 | Zdeblick et al. |
| 6,004,326 A | 12/1999 | Castro et al. |
| 6,042,582 A | 3/2000 | Ray |
| 6,063,088 A | 5/2000 | Winslow |
| 6,080,155 A * | 6/2000 | Michelson ................... 606/61 |
| 6,083,225 A | 7/2000 | Winslow et al. |
| 6,120,437 A | 9/2000 | Yoon et al. |
| 6,149,650 A | 11/2000 | Michelson |
| RE37,005 E | 12/2000 | Michelson et al. |
| 6,156,040 A | 12/2000 | Yonemura et al. |
| 6,165,219 A | 12/2000 | Kohrs et al. |
| 6,595,995 B2 * | 7/2003 | Zdeblick et al. .............. 606/80 |

FOREIGN PATENT DOCUMENTS

| | | |
|---|---|---|
| DE | 3505567 A1 | 11/1984 |
| DE | 4328690 A1 | 8/1993 |
| EP | 0 077 159 | 10/1981 |
| EP | 0 333 990 | 9/1989 |
| EP | 0 646 366 A1 | 4/1995 |
| EP | 0 676 176 A1 | 10/1995 |
| EP | 0796593 A2 | 9/1997 |
| FR | 2706309 | 6/1993 |
| FR | 2717068 | 3/1994 |
| WO | WO 91/06261 | 5/1991 |
| WO | WO 94/28824 | 12/1994 |
| WO | WO 94/11040 | 6/1995 |
| WO | WO 95/15133 | 6/1995 |
| WO | WO 96/22747 | 8/1996 |
| WO | WO 96/27345 | 12/1996 |
| WO | WO 96/40016 | 12/1996 |
| WO | WO 97/30666 | 8/1997 |

OTHER PUBLICATIONS

Scientix Brochure, Cage CH, "Lumbar Spacing Cages", Mar. 9, 1999.

*Intervertebral Body Fusion By the Use of Posterior Bone Dowel*, Benjamin R. Wilterberger, M.D., pp. 69-79, Mar. 9, 1999.

*A Technique of Posterior Cervical Fusion for Instability of the Cervical Spine*, Davey et al. (1984).

Surgical Dynamics Brochure, Ray Ti for Interbody Fusion, Investigational Device, (1984).

Stryker Implants Brochure, Ogival Interbody Cage, Surgical Technique, Dec. 1, 1995.

*Unilateral Posterior Lumbar Interbody Fusion; Simplified Duel Technique*, Blume (1984).

*Laparoscopic Bone Dowel Surgical Technique*, Sofamor Danek, The Spine Specialist, 1995.

*Laparoscopic Bone Dowel Instruments*, Sofamor Danek, The Spine Specialist, 1995.

*Current Concepts in Spinal Endoscopy*, 1995 Course Schedule, Medical Education and Research Institute, Funded by Methodist Health Systems & Semmes Murphey Clinic.

\* cited by examiner

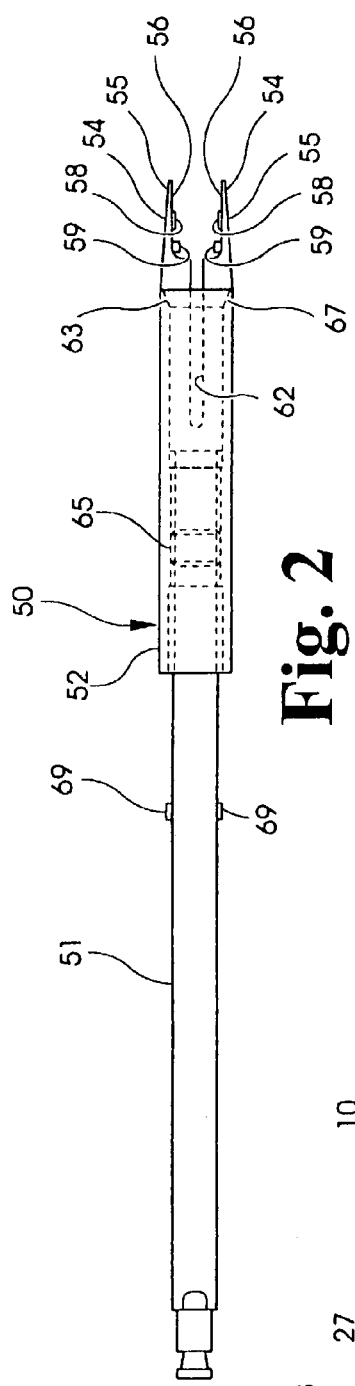
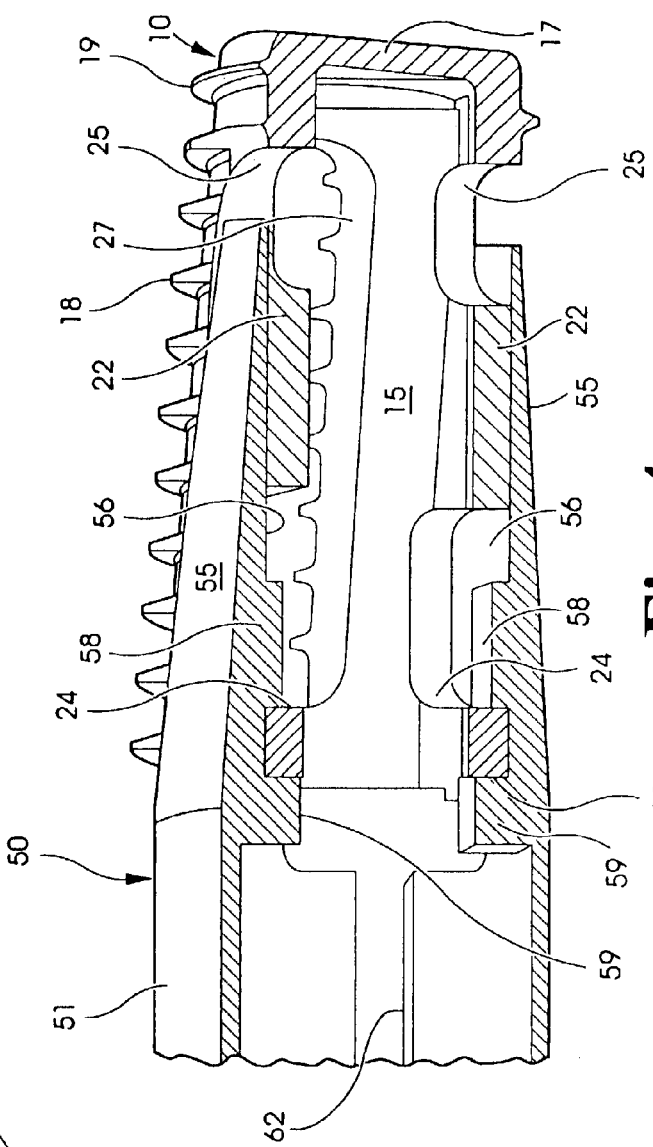
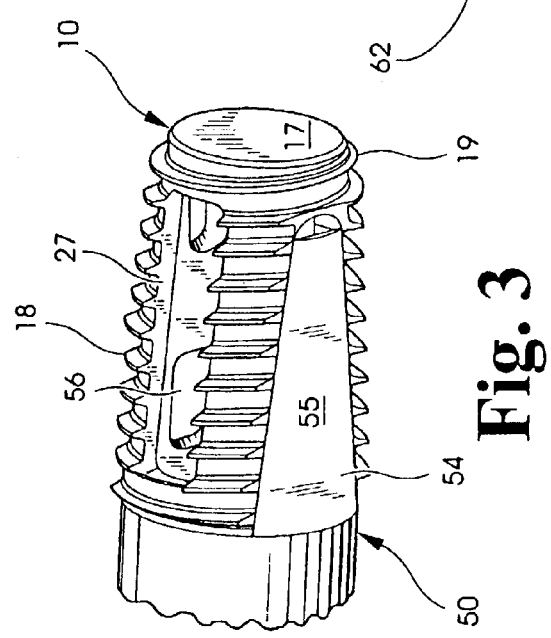

1. Dilate the disc space (slight lordosis):

2. Place outer sleeve & drill minor diameter hole:

3. Insert implant to secure lordosis required

4. Remove implant driver

1. Dilate the disc space:

2. Place outer sleeve & drill minor diameter hole:

3. Insert implant to appropriate depth

4. Rotate to restore lordosis, remove implant driver

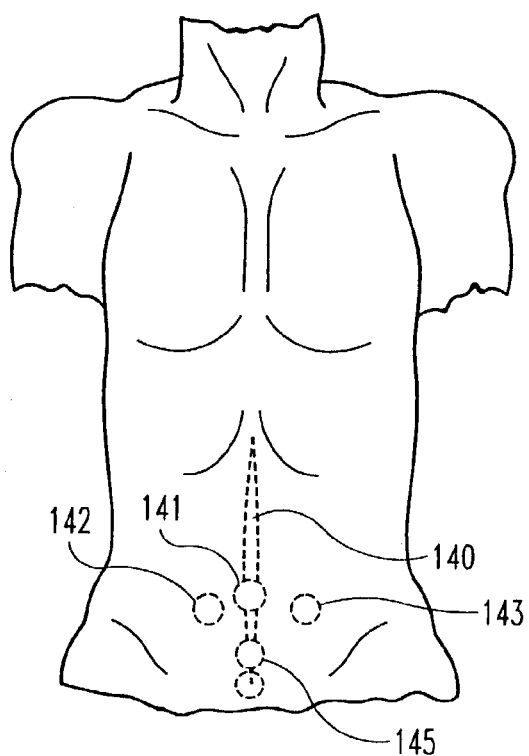
Fig. 10
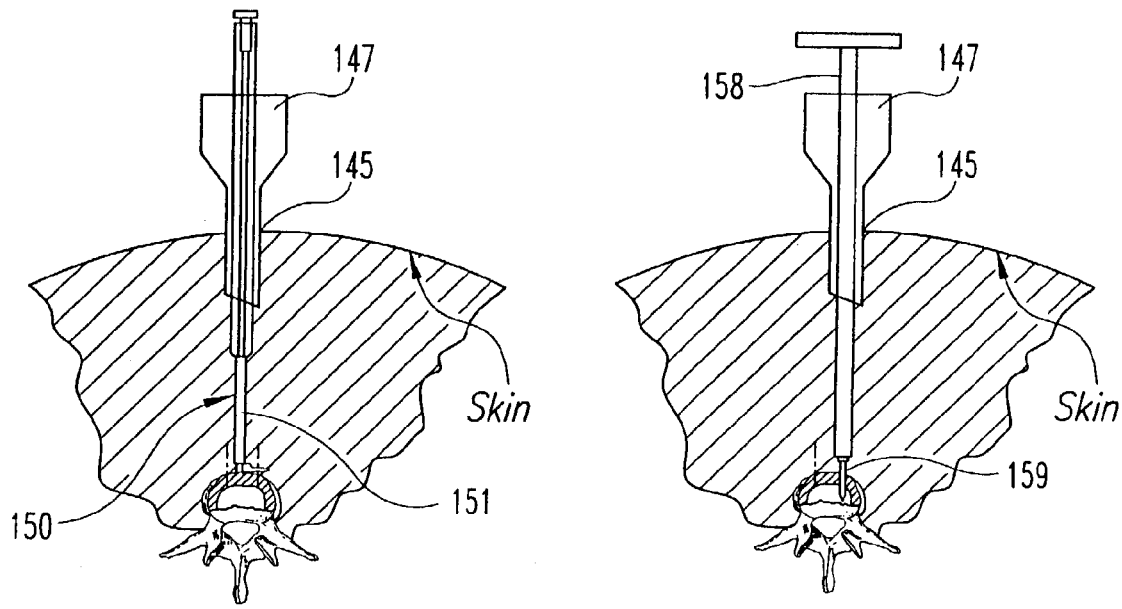
Fig. 11     Fig. 13

METHODS AND INSTRUMENTS FOR INTERBODY FUSION

BACKGROUND OF THE INVENTION

This application is a continuation of U.S. patent application Ser. No. 09/746,300, filed Dec. 21, 2000 now U.S. Pat. No. 6,595,995, which is a continuation of U.S. patent application Ser. No. 09/265,179, filed Mar. 9, 1999, now U.S. Pat. No. 6,245,072, issued Jun. 12, 2001, which is a continuation of U.S. patent application Ser. No. 09/176,972, filed Oct. 22, 1998, now abandoned, which is a continuation of U.S. patent application Ser. No. 08/604,874, filed Feb. 22, 1996, now abandoned, which is a continuation-in-part of U.S. Pat. No. 08/411,017, filed Mar. 27, 1995, now U.S. Pat. No. 5,782,919, issued Jul. 21, 1998.

The present invention relates to methods and instruments for performing an interbody fusion of a disc space between two adjacent vertebrae. Specifically, the invention concerns laparoscopic techniques and instruments to prepare a fusion site and to insert fusion devices and implants.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intra-discal space, otherwise the space may collapse resulting in damage to the nerves extending along the spinal column.

The intra-discal space is often filled with bone or a bone substitute in order to prevent disc space collapse and to promote fusion of the two adjacent vertebrae. In early techniques, bone material was simply disposed between the adjacent vertebrae, typically at the posterior aspect of the vertebrae, and the spinal column was stabilized by way of a plate or a rod spanning the affected vertebrae. Once fusion occurred the hardware used to maintain the stability of the segment became superfluous. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intra-discal implant that could be used to replace a damaged disc and maintain the stability of the disc interspace between the adjacent vertebrae, at least until complete arthrodesis is achieved. These "interbody fusion devices" have taken many forms. For example, one of the more prevalent designs takes the form of a cylindrical implant. These types of implants are. disclosec in the patents to Bagby, U.S. Pat. No. 4,501,269; Brantigan, U.S. Pat. No., 4,878,915; Ray, U.S. Pat. Nos. 4,961,740 and 5,055,104; and Michelson, U.S. Pat. No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intra-discal space and the vertebral end plates. These types of devices are represented by the patents to Brantigan, U.S. Pat. Nos. 4,743,256; 4,834,757 and 5,192,327.

Interbody fusion devices can be generally divided into two basic categories, namely solid implants and implants that are designed to permit bone ingrowth. Solid implants are represented by U.S. Pat. Nos. 4,878,915; 4,743,256; 4,349,921 and 4,714,469. The remaining patents discussed above include some aspect that permits bone to grow across the implant. It has been found that devices that promote natural bone ingrowth achieve a more rapid and stable arthrodesis. The device depicted in the Michelson '247 Patent is representative of this type of hollow implant which is typically filled with autologous bone prior to insertion into the intra-discal space. This implant includes a plurality of circular apertures which communicate with the hollow interior of the implant, thereby providing a path for tissue growth between the vertebral end plates and the bone or bone substitute within the implant. In preparing the intra-discal space, the end plates are preferably reduced to bleeding bone to facilitate this tissue ingrowth. During fusion, the metal structure provided by the Michelson implant helps maintain the patency and stability of the motion segment to be fused. In addition, once arthrodesis occurs, the implant itself serves as a sort of anchor for the solid bony mass.

Another interbody fusion device that is designed to permit bone ingrowth is shown in FIG. 1. This device is described and claimed in co-pending parent application Ser. No. 08/411,017, filed on Mar. 27, 1995, which disclosure is incorporated herein by reference. In one embodiment, this invention contemplates a hollow threaded interbody fusion device 10 configured to restore the normal angular relation between adjacent vertebrae. In particular, the device 10 as shown in FIG. 1 includes an elongated body 11, tapered along substantially its entire length, defining a hollow interior 15 and having a largest outer diameter at the anterior end 12 greater than the size of the space between the adjacent vertebrae. The hollow interior 15 opens at the anterior end 12 od the device to receive the bone growth material. The body 11 includes an outer surface 16 with opposite tapered cylindrical portions and a pair of opposite flat tapered side surfaces 22 between the cylindrical portions. Thus, at an end view, the fusion device gives the appearance of a cylindrical body in which the sides of the body have been truncated along a chord of the body's outer diameter.

The cylindrical portions include threads 18 for controlled insertion and engagement into the end plates of the adjacent vertebrae. A starter thread 19 is provided at the posterior end 13 of the device 10 to facilitate engagement within a prepared bore. The outer surface of this fusion device is tapered along its length at an angle corresponding, in one embodiment, to the normal lordotic angle of lower lumbar vertebrae. The outer surface is also provided with a number of vascularization openings 24, 25 defined in the flat side surfaces, and a pair of opposite elongated bone ingrowth slots 27 defined in the cylindrical portions.

Various surgical methods have been devised for the implantation of fusion devices into a subject disc space. A patent to Dr. Gary Michelson, U.S. Pat. No. 5,484,437, discloses one such technique and the associated instruments. As described in more detail in that patent, the surgical technique involves the use of a hollow sleeve having teeth at one end that are driven into the adjacent vertebrae. These teeth and the sleeve maintain the disc space height during the subsequent steps of the procedure. In accordance with one aspect of the invention in the '437 Patent, a drill is passed through the hollow sleeve to remove the disc and bone material to produce a prepared bore for the fusion device. The drill is then removed from the sleeve and the fusion device is positioned within the disc space using an insertion tool.

In another aspect of the procedure and instruments disclosed in the '437 Patent, a long distractor is provided having penetrating portions that urge the vertebral bodies apart to facilitate the introduction of the necessary instruments. The long distractor can act as a guide for drilling and reaming tools concentrically advanced over the outside of the distractor to prepare the site for the fusion device.

While the Michelson technique represents a significant advance over prior surgical procedures for the preparation and insertion of fusion devices, the need for improvement remains. In particular, procedures and instruments that preserve the integrity of the surgical site are desirable. The present invention is directed to this need in the field.

DESCRIPTION OF THE FIGURES

FIG. 2 is a top elevational view of an implant driver for use in engaging and driving a fusion device such as the device shown in FIG. 1.

FIG. 3 is an enlarged perspective view of the end of the implant driver shown in FIG. 2 engaged to an fusion device such as shown in FIG. 1.

FIG. 4 is an enlarged side cross-sectional view of the implant driver and fusion device shown in FIG. 3.

FIG. 10 is a frontal view of a patient with locations identified for surgical incisions according to a preferred embodiment of the present inventive laparoscopic surgical technique.

FIG. 11 is an A-P representation of a spinal segment at the laparoscopic surgical site depicting one step of the inventive surgical technique in which bilateral locations are marked on the disc annulus for insertion of a pair of fusion devices, such as the device shown in FIG. 1.

FIG. 13 is an A-P representation of the laparoscopic surgical site depicting a further step of the inventive surgical technique of creating a pilot hole at each of the bilateral locations marked in the step shown in FIG. 11.

SUMMARY OF THE INVENTION

Figure 1:
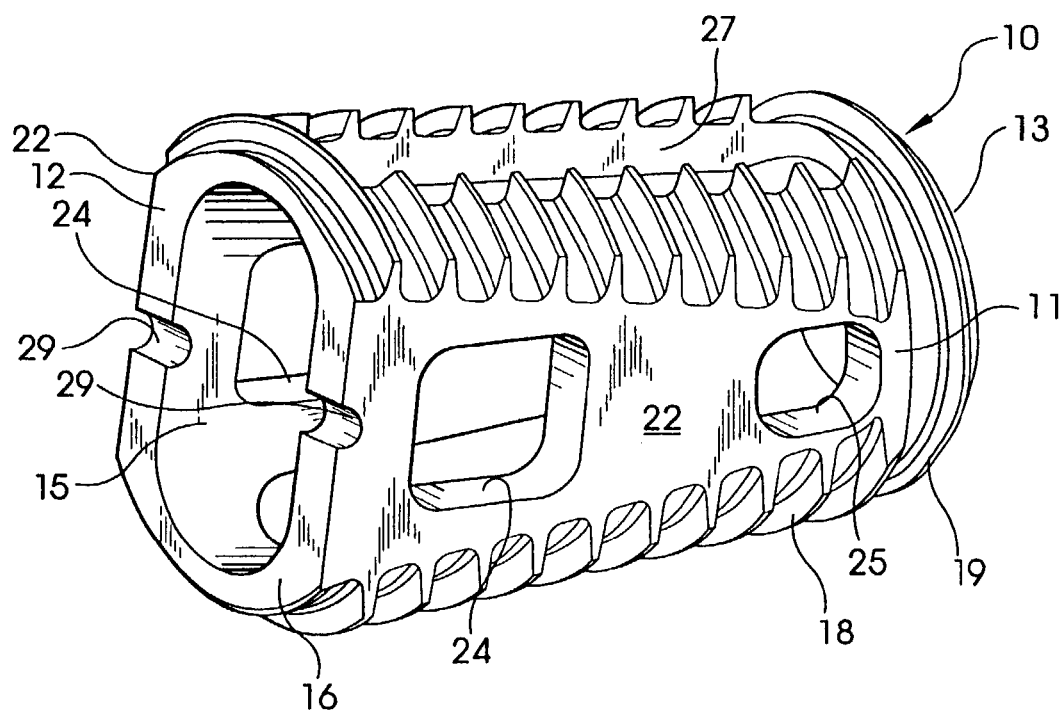
FIG. 1 is a side perspective view of a threaded fusion device having a tapered configuration to restore the normal angle of a spinal motion segment.

In accordance with one aspect of the invention, a driving tool assembly for implanting an interbody fusion device in the space between adjacent vertebrae is provided. The fusion device including a body has a cylindrical outer surface interrupted by opposite non-cylindrical side walls, the outer surface having external threads defined thereon for threading into the adjacent vertebrae. The tool assembly comprises a driving tool including an elongated shaft and a pair of opposite tongs connected to one end of said shaft. The tongs are disposed apart relative to each other to receive the opposite side walls of the fusion device therebetween. In accordance with the invention, a driving tool attachment includes a body having an outer surface and first and second ends. The body defines opposite non-cylindrical walls in its outer surface at the first end, with the walls configured for clamping engagement between the tongs of the driving tool. The body further defines opposite flanges extending from its second end, the opposite flanges having facing surfaces configured to engage the side walls of the fusion implant therebetween to impart a driving force from said driving tool attachment to the fusion implant when the driving tool attachment is engaged to said driving tool.

In another aspect of the invention, a method is provided for preparing a subject disc space for implantation of a fusion device or implant between adjacent vertebrae. In this technique, a laparoscope is provided that includes an outer sleeve with opposite extensions at one end of the outer sleeve and a laparoscopic port engaged at the other end of the outer sleeve, the laparoscopic port having a number of seals, with the opposite extensions configured to maintain distraction of the adjacent vertebrae.

The preferred technique comprises the steps of making an incision in the skin of the patient aligned with the subject disc space, retracting tissue beneath the incision to expose the disc annulus; and piercing the disc annulus to create an opening. The the outer sleeve of the laparoscope is advanced through the incision, leaving the port outside the skin of the patient while inserting the opposite extensions into the disc space with the outer sleeve contacting the disc annulus. The laparoscope, and particularly, the outer sleeve, creates a protected working channel between the disc space and the laparoscopic port outside the patient.

In a further step of the preferred inventive technique, a reamer is operated through the number of seals and the outer sleeve of the laparoscope to create a prepared bore in the disc material and the adjacent vertebrae for implantation of a device into the bore.

In a most preferred embodiment of the surgical technique, the technique comprises the steps of percutaneously exposing the annulus of the disc in the subject disc space through an incision in the skin of the patient and piercing the disc annulus to create an opening. A distractor can then be inserted through the incision and through the opening into the disc space to distract the vertebrae adjacent the subject disc space. The laparoscope outer sleeve is then introduced through the incision and over the distractor, leaving the port outside the skin of the patient while inserting the opposite extensions through the opening into the disc space to create the protected working channel between the port and the distractor tip.

In subsequent steps, the distractor is removed and a reamer is advanced through the number of seals of the laparoscope and through the outer sleeve into the disc space to ream the disc space and adjacent vertebrae to create a prepared bore for the fusion implant. After the reamer is removed from the laparoscope, the fusion implant can be advanced through the number of seals and through the outer sleeve into the prepared bore. With the fusion implant in position, the laparoscope can be withdrawn from the patient.

In one aspect of the invention, a switching sleeve is palced within the outer sleeve of the laparoscope with an end of the switching sleeve projecting beyond the opposite fingers of the outer sleeve, the end of the switching sleeve being tapered to minimize trauma to tissue adjacent the subject disc space as the outer sleeve advanced into the patient with the switching sleeve projecting beyond the opposite extensions of the outer sleeve.

In a further embodiment, the laparoscopic method is used for bilateral placement of two fusion devices into a subject disc space. In addition to the steps previously described, this embodiment of the surgical technique includes unseating the outer sleeve of the laparoscope from the first opening in the disc annulus by withdrawing the laparoscope until the opposite extensions of the outer sleeve are outside the disc annulus. With the switching sleeve in position within the outer sleeve, the laparoscope is moved to the second opening in the disc space without removing the laparoscope from the patient. The steps for preparing the bore to receive a fusion implant can be repeated. In one specific embodiment, these steps are conducted at the second opening with the distractor remaining within the first opening. After a fusion implant isnced through the number of seals and through the outer sleeve into the second prepared bores the laparoscope can then be returned to the first opening for insertion of another fusion implant. During this step, the fusion implant contained within the second prepared bore maintains distraction of the disc space.

One object of the present invention is to provide surgical technique and instruments that permit the preparation of a disc space for insertion of a fusion implant under a sealed condition. A further object of the invention is to implement laparoscopic techniques to implant fusion devices.

One benefit of the present invention is that all of the steps necessary to prepare a disc space and to implant a fusion device can be conducted in a protected environment. In addition, the inventive techniques and instruments allow minimal intrusion into the patient, which minimizes the risks normally associated with spinal surgery.

Other objects and benefits can be discerned from the following written description and accompanying figures.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

As described above, one interbody fusion device, as shown in FIG. 1, can be implanted within the intra-discal space. This interbody fusion device 10 can be implanted using the implant driver 50 shown in FIG. 2. The implant driver 50 is comprised of a shaft 51 and sleeve 52 concentrically disposed about the shaft. Tongs 54 are formed at one end of the shaft for gripping the interbody fusion device 10 for implantation. Preferably the tongs include a tapered outer surface 55 and an opposite flat inner surface 56 adapted to engage the truncated side walls 22 of the interbody fusion device as shown in FIGS. 3, 4. Most preferably the tapered outer surface 55 conforms to the root diameter of the interrupted threads 18 of the device 10 so that the tongs 54 essentially complete the full cylindrical shape of the body wall 16. The adaptation of the tongs' tapered outer surface 55 facilitates screw insertion of the interbody fusion device 10 since the outer surface 55 will ride within the tapped bore in the vertebral end plates.

Each of the tongs 54 can be provided with interlocking fingers 58 and a driving projection 59 extending from the inner surface 56, most clearly shown in FIG. 4. Referring again to FIG. 2, the shaft 51 defines a hinge slot 62 supporting each of the pair of tongs 54. The hinge slot 62 is configured so that the tongs will have a naturally biased position spread sufficiently apart to accept the fusion device 10 therebetween. The shaft 51 defines a conical taper 63 between the hinged slot 62 and each of the tongs 54. This conical taper mates with a conical chamfer 67 defined on the inner wall of the sleeve 52. Thus, as the sleeve 52 is advanced toward the tongs 54, the conical chamfer 67 rides against the conical taper 63 to close or compress the hinge slot 62. In this manner, the tongs 54 are pushed toward each other and pressed into gripping engagement with the interbody fusion device situated between the tongs.

The shaft 51 and sleeve 52 are provided with a threaded interface 65 which permits the sleeve 52 to be threaded up and down the length of the shaft. Specifically, the threaded interface 65 includes external threads on the shaft 51 and internal threads on the sleeve 52 having the same pitch so that the sleeve can be readily moved up and down the implant driver 50. The shaft 51 is also provided with a pair of stops 69 which restrict the backward movement of the sleeve 52 to only the extent necessary to allow the tongs 54 to separate a sufficient distance to accept the interbody fusion device 10.

The use of the implant driver 50 is shown with reference to FIGS. 3, 4. As can be seen in FIG. 3, the outer surface 55 of the tongs 54 reside generally flush with the root diameter of the interrupted threads 18. As seen in FIG. 4, the interlocking fingers 58 can be arranged to fit within the vascularization opening 24 on each of the truncated side walls 22. In a similar fashion, the driving projections 59 engage the driving tool slots 29 at the anterior end 12 of the conical body 11. The combination of the interlocking fingers 58 and driving projections 59 firmly engage the interbody fusion device 10 so that the device can be screw threaded into a tapped or untapped opening in the vertebral bone. The tongs 54 in this embodiment are configured to engage the fusion device 10 and to impart a threading or rotational force to the device. It is understood that the tongs can adopt other configurations depending upon the structure of the fusion device to be implanted.

Figure 5:
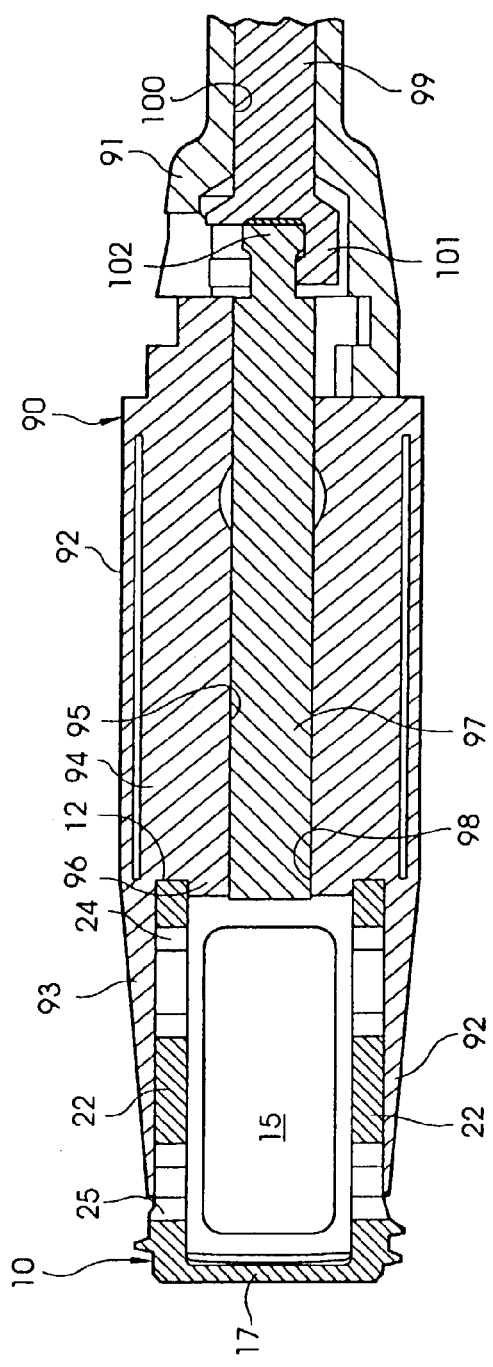
FIG. 5 is an enlarged side cross-sectional view of an alternative embodiment of an implant driver for engaging and driving a fusion device such as the device shown in FIG. 1.

An alternative embodiment of the implant driver is shown in FIG. 5. The driver 90 includes a shaft 91, having a length sufficient to reach into the intra-discal space from outside the patent. Connected to the end of shaft 91 is a head which defines a pair of opposite tongs 93, each of which are configured for flush contact with the flat truncated side walls 22 of the fusion device 10. Like the tongs 54 of the previously described implant driver 50, the outer surface of the tongs is cylindrical to correspond to the cylindrical threaded portion of the device.

Unlike the implant driver 50, the driver 90 of the embodiment in FIG. 5 uses an expanding collet assembly to firmly grip the fusion device 10 for insertion into the body. Specifically, the head 92 defines a collet 94 having a central collet bore 95 formed therethrough. The collet 94 terminates in an annular flange 96 that at least initially has a diameter slightly smaller than the inner diameter of the fusion device 10 at its end 12. An expander shaft 97 slidably extends through the collet bore and includes a flared tip 98 situated adjacent and extending just beyond the annular flange 96. The flared tip 98 of the expander shaft 97 starts at a diameter sized to slide within the collet bore 95 and gradually flares to a diameter larger than the bore.

The implant driver 90 further includes a puller shaft 99 slidably disposed within a bore 100 defined in the shaft 91. The puller shaft 99 has a locking chamber 101 at its end which engages a locking hub 102 formed at the end of the expander shaft 97. The puller shaft 99 projects beyond the end of the shaft 91 for access by the surgeon. When the puller shaft 99 is pulled, it pulls the expander shaft 97 away from the annular flange 96 of the collet 94 so that the flared tip 98 becomes progressively engaged within the collet bore 95. As the tip 98 advances further into the bore 95, the annular flange 96 expands from its initial diameter to a larger second diameter sufficient for firm gripping contact with the interior of the fusion device 10. With the fusion device so engaged, the implant driver can be used to insert the device 10 into the surgical site, after which the expander shaft can be advanced beyond the collet bore to release the flat tip and, consequently, the fusion device.

Figure 6:
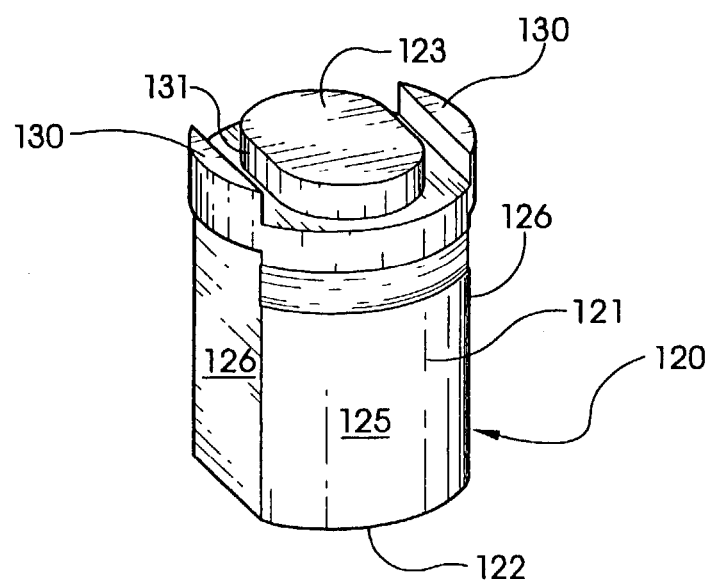
FIG. 6 is a driving tool attachment according to on aspect of the present invention.

In certain circumstances it may be necessary to drive the fusion device 10 deeper into the disc space. When either of the implant drivers 50 or 90 is engaged to the fusion device, the device can be readily advanced farther into the disc space. However, onse the implant driver is removed and it is then discovered that the fusion device needs to be repositioned, the flexible nature of the tongs 54 and 93 of the two implant drivers makes reacquisition of the now implanted fusion device difficult. To alleviate this difficulty, a driving tool attachment 120 is provided, as shown in FIG. 6. The driving tool attachment 120 includes a body 121 having a first end 122 and an opposite second end 123. Like the fusion implant, the body 121 of the driving tool attachment 120 includes a cylindrical portion 125 and opposite flat side portions 126. The opposite side portions 126 are configured to be engaged by the tongs of the above driving tools 50 or 90.

The driving tool attachment 120 includes a pair of opposing flanges 130 at end 123. The flanges 130 are configured to engage the opposite flat surfaces 122 on the fusion implant 10, in a manner similar to that accomplished by the tongs of the implant driver 50 and 90. The end 123 also includes a boss 131 which is configured to be inserted into the opening at the end of the implant 10 (see FIG. 7).

Figure 7:
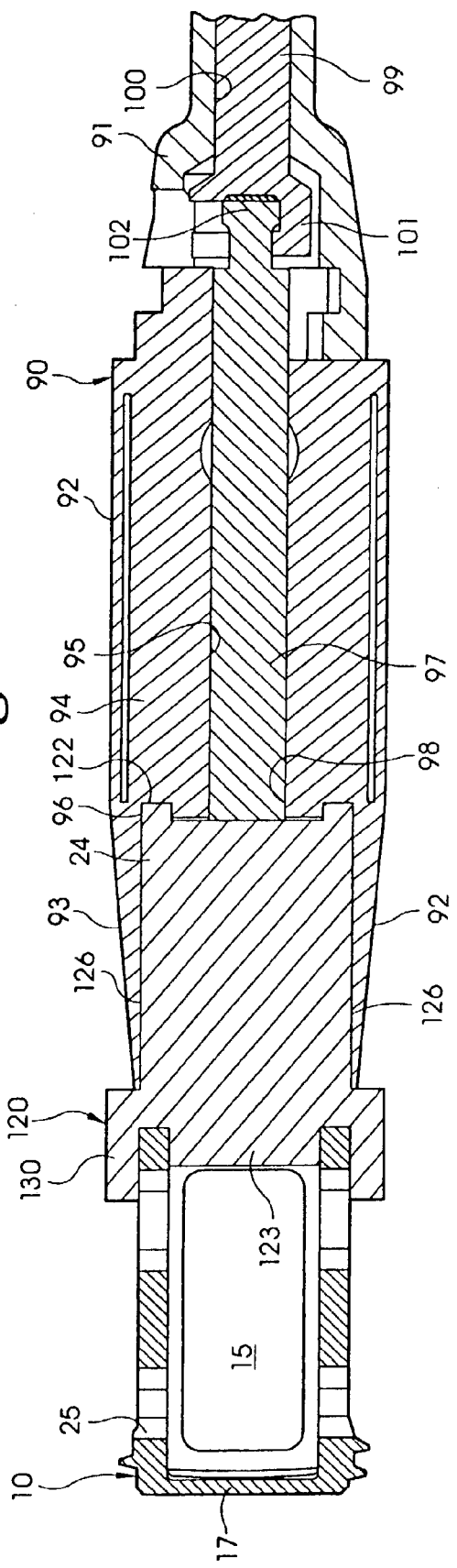
FIG. 7 is an enlarged side cross-sectional view similar to the view in FIG. 5 with the driving tool attachment of FIG. 6 engaged between the implant driver and the fusion device.

In use, the driving tool attachment 120 can be engaged with one of the driving tools 50 or 90, with the tongs firmly grasping the flat surfaces 126, as shown in FIG. 7. The driving tool attachment can then be advanced into the disc space with the flanges 130 oriented across the space so that they can readily interface with the flat surfaces 22 of the fusion device 10. When the driving tool attachment 120 is properly aligned, the boss 131 projects into the hollow opening 15 at the anterior end 12 of the fusion device and the flanges 130 engage the opposite flat surfaces 22 of the device. The driving tool can then be rotated as if the fusion implant were directly engaged to the main driving tool. The attachment readily transmits the rotational driving force to the implant 10 to thread it deeper into the disc space or to retract it back within the disc space. One particular advantage provided by the driving tool attachment 120 is that the relatively flexible tongs of the two driving tools 50 and 90 can be already engaged to the attachment 120 before insertion into the surgical site. This eliminates a great deal of fiddle factor and avoids the risk that the tongs would be unable to firmly grasp the implant 10 when it is already in position within the disc space.

Figure 8A:
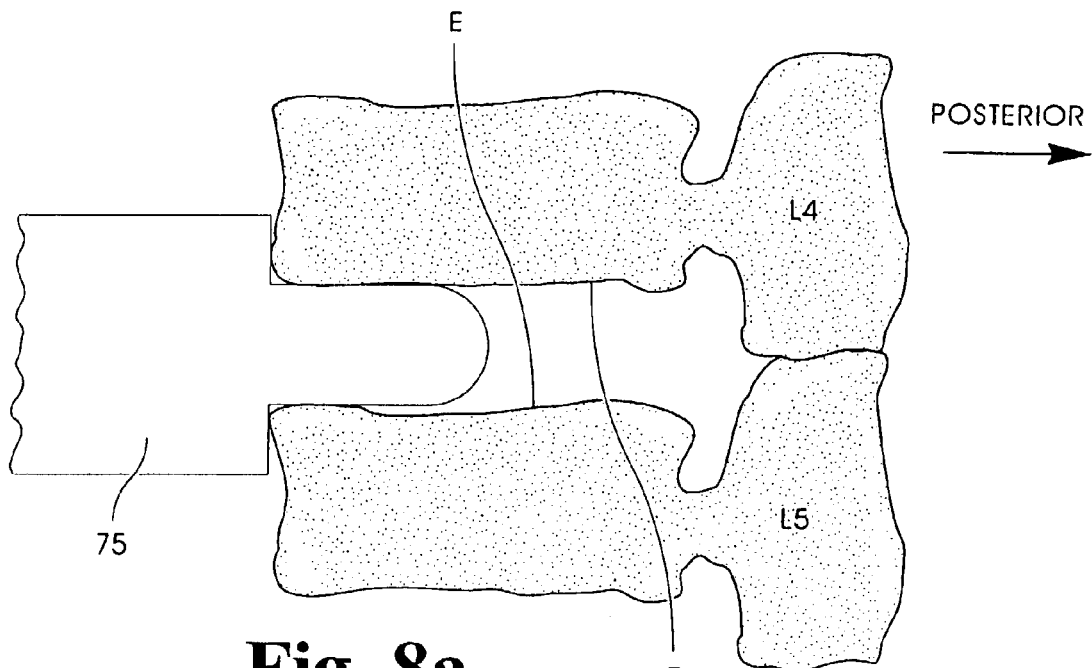
FIGS. 8(a)-(d) are lateral representations of the spine showing four steps of a surgical method for implanting a fusion device such as the device in FIG. 1 according to an anterior approach in one aspect of the present invention.
Figure 8B:
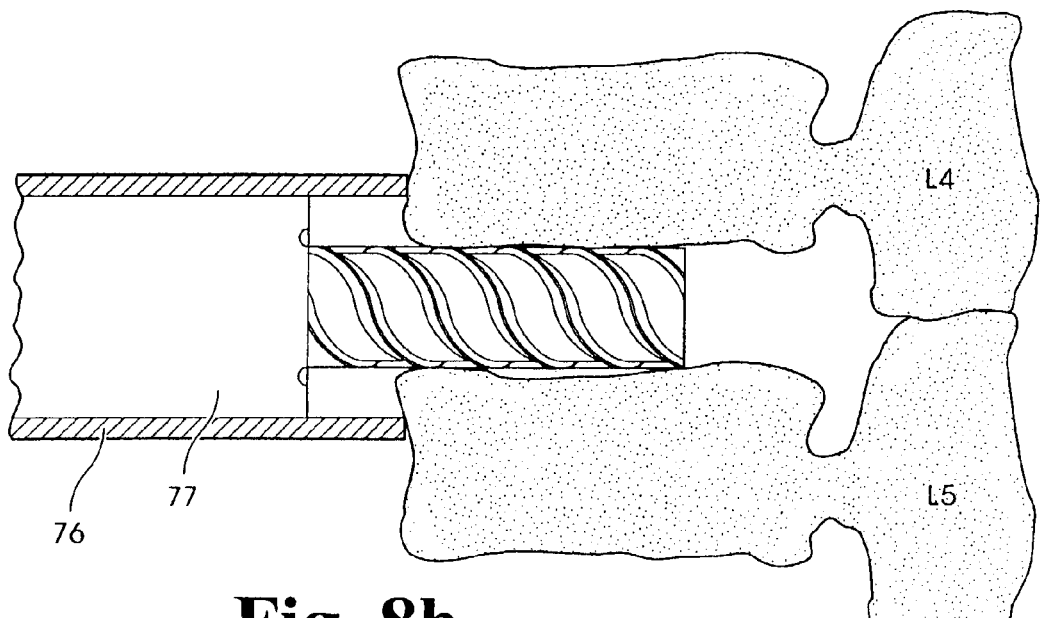

In accordance with additional aspects of the present invention, two methods for implanting an interbody fusion device, such as the device 10, are contemplated. First, with reference to FIGS. 8(a)-8(d), an anterior approach is shown. As a preliminary step, it is necessary to locate appropriate starting points for implanting the fusion device, preferably bilaterally. In the first step of the anterior approach, a distractor 75 is disposed between the vertebral end plates E to dilate the L4-L5 or L5-S1 disc space. (It is understood, of course, that this procedure can be applied at other vertebral levels). In the second step, shown in FIG. 8(b), an outer sleeve 76 is disposed about the disc space. The outer sleeve 76 can be configured to positively engage the anterior aspect of the vertebral bodies to firmly, but temporarily, anchor the outer sleeve 76 in position. In essence, this outer sleeve 76 operates as a working channel for this approach. In the step of FIG. 8(b), a drill 77 of known design is extended through the outer sleeve and used to drill out circular openings in the adjacent vertebral bodies. The openings can be tapped to facilitate screw insertion of the fusion device 10, although this step is not necessary.

Figure 8C:
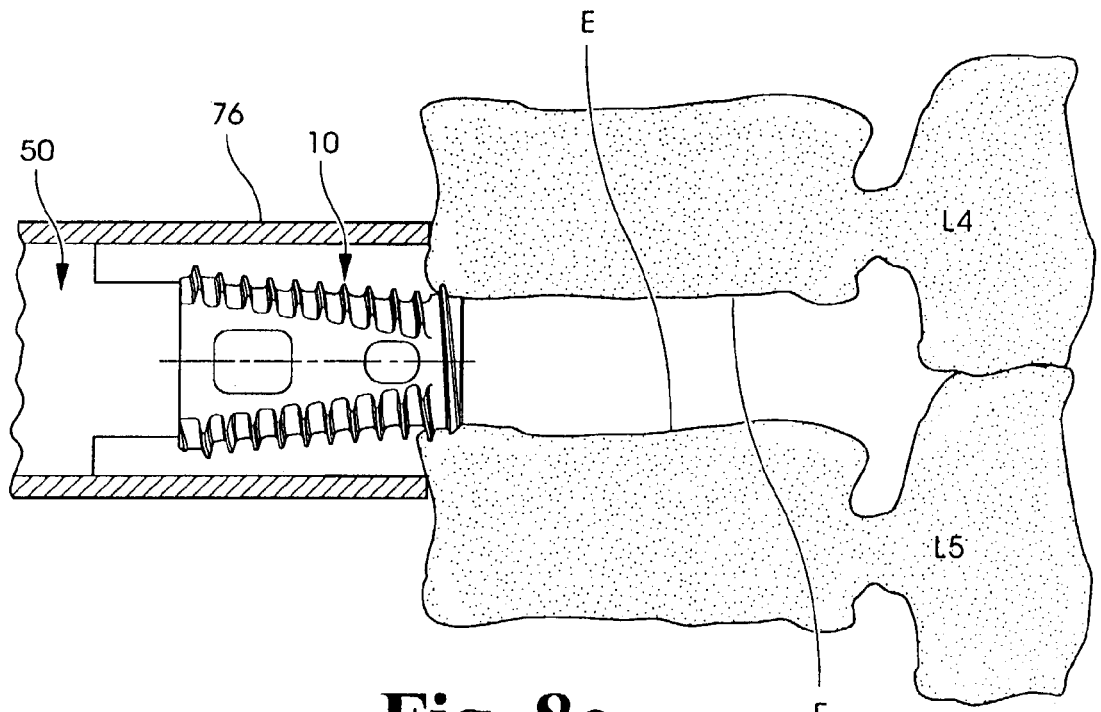
Figure 8D:
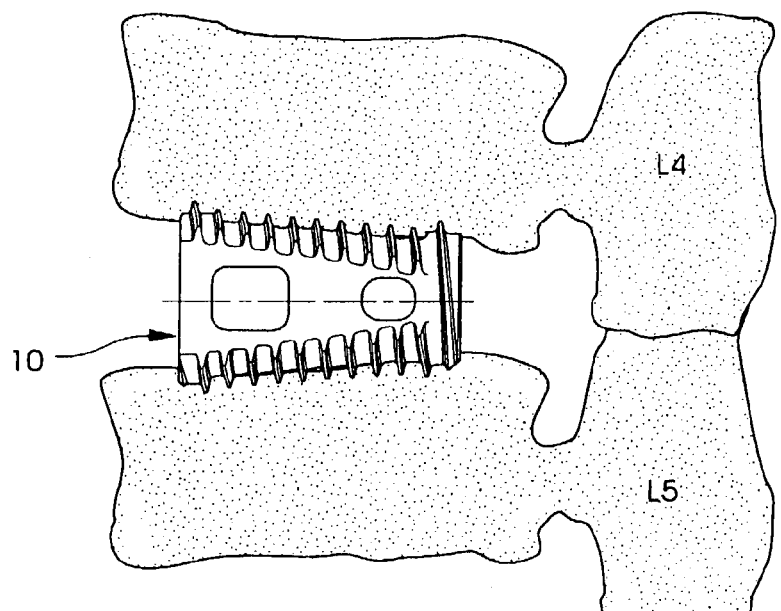
Figure 9A:
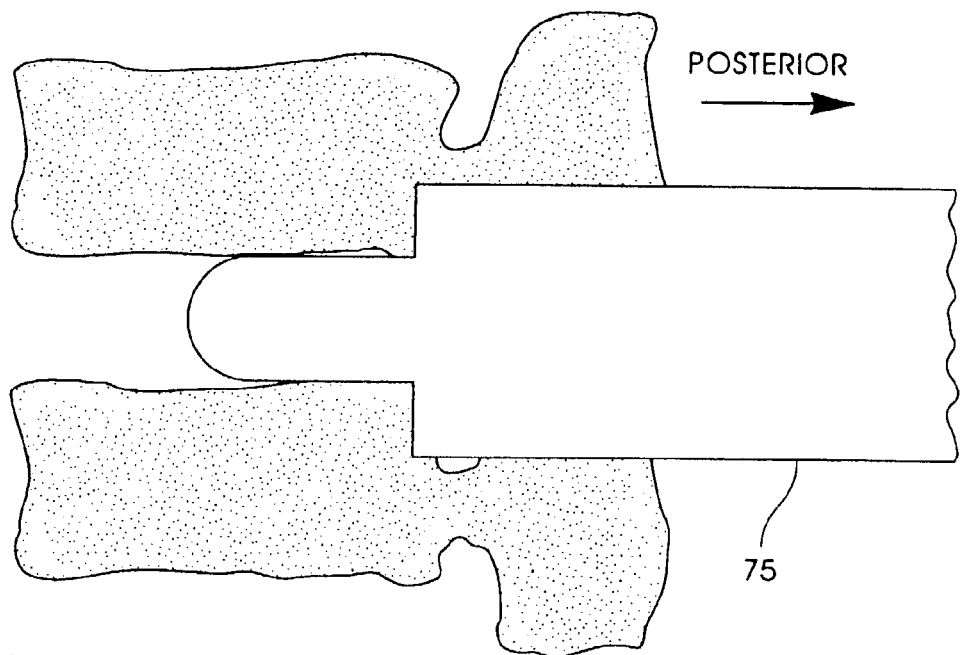
FIGS. 9(a)-(d) are lateral representations of the spine showing four steps of a surgical method for implanting a fusion device such as the device in FIG. 1 according to a posterior approach in further aspect of the present invention.
Figure 9B:
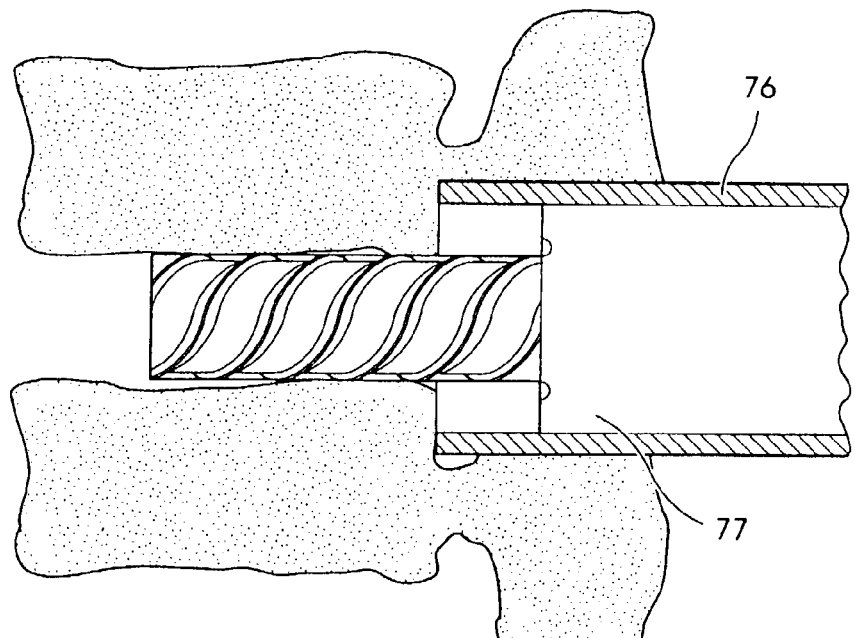
Figure 9C:
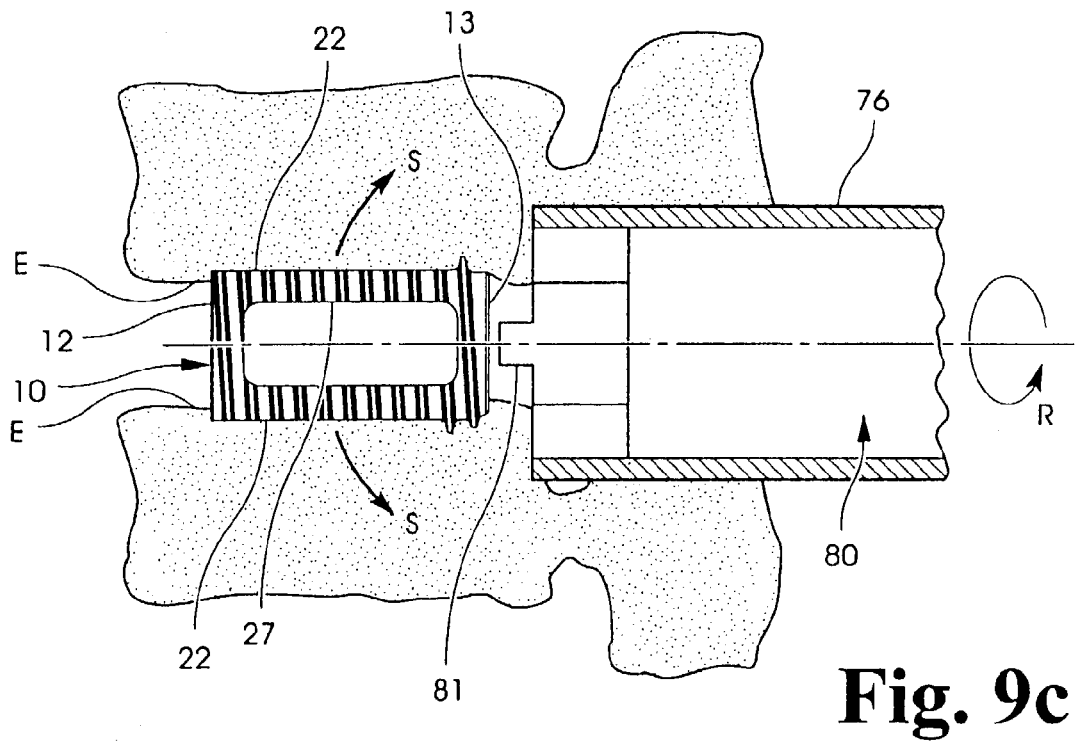
Figure 9D:
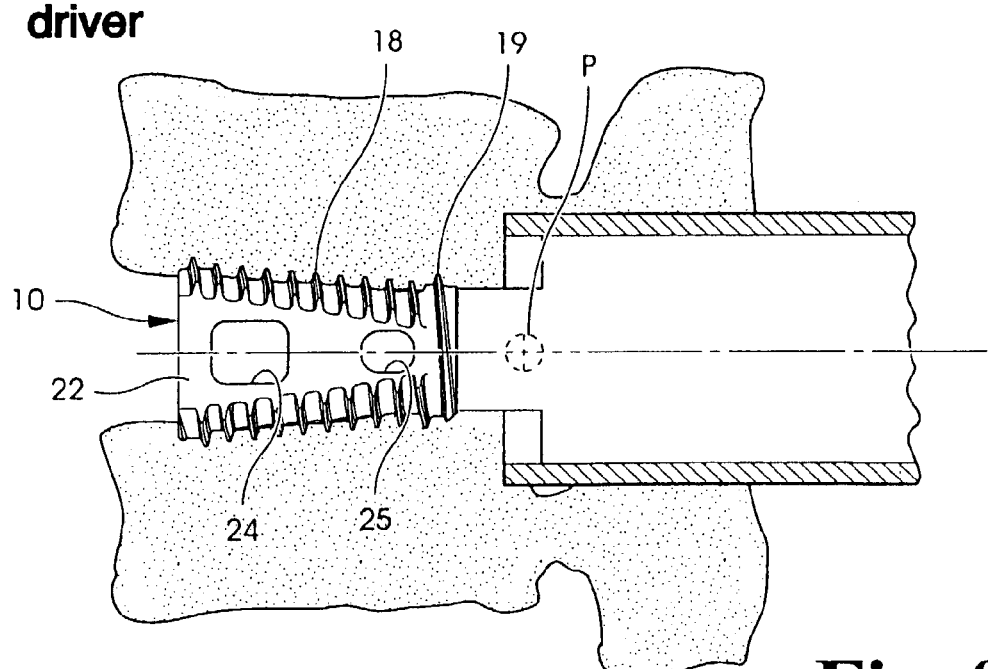

In the next step shown in FIG. 8(c), the fusion device 10 is engaged by the implant driver 50 and extended through the outer sleeve 76 until the starter thread 19 contacts the bone opening. The implant driver 50 can then be used to screw thread the fusion device into the tapped or untapped opening formed in the vertebral end plate E. It is understood that in this step, other suitable driving tools could be used, such as a screw driver configured to engage the driving tool slots 29 at the anterior end 12 of the device 10. The degree of insertion of the fusion device 10 determines the amount of lordosis added or restored to the vertebral level. In the final step, the implant driver is removed leaving the fusion device 10 in position. It can be seen that once implanted, the closed posterior end 13 is directed toward the posterior aspect of the vertebrae. The hollow interior 15 is open at its anterior end 12, but can be closed by a plastic or metal material, if necessary.

In a second inventive method, as depicted in FIGS. 9(*a*)-9(*d*), a posterior approach is implemented. The first two steps of the posterior approach are similar to that of the prior anterior approach, except that the distractor 75, outer sleeve 76 and drill 77 are introduced posteriorly at the instrumented motion segment. This approach may require decortication and removal of vertebral bone to accept the outer sleeve 76. In the third step of this method, the fusion device 10 is inserted through the outer sleeve 76 into the dilated disc space. It is understood that the disc space is preferably dilated only to the extent necessary to receive the implant with the truncated side walls 22 directly facing the vertebral end plates E. Thus, as shown in FIG. 9(*c*), the bone ingrowth slot 27 is facing laterally, rather than coronally, as expected for its final implanted position. A suitable driving tool 80 can be provided to project the fusion device 10 through the outer sleeve 76 and into the intra-discal space. In one embodiment, the driving tool 80 includes a projection 81 which is configured to engage a slot opening formed in the end wall at the posterior end 13 of the fusion device 10. An internal thread (not shown) can be used to fix the device 10 to the driver 80.

Once the fusion device 10 has been advanced into the intra-discal space to the appropriate depth relative to the pivot axis P of the vertebrae, the driving tool 80 is used to rotate the implant in the direction of the rotational arrow R in FIG. 9(*c*). As the driving tool 80 is rotated, the device itself rotates so that the interrupted threads 18 start cutting into the vertebral bone at the end plates E. In this manner, the implant operates as a cam to separate the adjacent vertebrae in the direction of the spreading direction arrows S in FIG. 9(*c*). This camming approach provides a somewhat easier insertion procedure than for the anterior approach of FIGS. 8(*a*)-(*d*) in that a single rotation is required to lock the implant into the vertebral bone. In contrast, the formerly discussed screw insertion technique of the anterior approach requires continuous threading of the device into position.

With either the anterior (FIGS. 8(*a*)-(*d*)) or the posterior approach (FIGS. 9(*a*)-(*d*)), the position of the fusion device 10 with respect to the adjacent vertebrae can be verified by radiograph or other suitable techniques for establishing the angular relationship between the vertebrae. Alternatively, the preferred depth of insertion of the implant can be determined in advance and measured from outside the patient as the implant is positioned between the vertebrae. The depth of insertion of the fusion device can be ascertained using depth markings (not shown) on the implant drivers 50, 90 or 80.

In another embodiment of the inventive surgical technique, laparoscopic technology is used to provide a sealed and protected channel for instruments and implants directed to the subject disc space. In accordance with one aspect of this inventive method, an anterior approach to the L5-S1 motion segment is illustrated. It is of course understood that these same techniques and instruments to be described below could be used at different vertebral levels or in a posterior approach under appropriate conditions.

As depicted in FIG. 10, the present inventive technique includes making a small incision 140 and preferably inserting an insufflator needle into the abdominal cavity. Fluid is introduced into the abdominal cavity through the insufflator needle to a pressure of preferably approximately 15 mm of mercury to assist in visualization of the surgical site. An initial port 141 for the laparoscope is placed five to ten centimeters cephalad of the umbilicus in the midline ten millimeters in length. The abdomen is visually explored and the patient is placed in steep Trandelenburg. The abdominal wall is visualized endoscopically as two working ports 142, 143 are placed just lateral to the epigastric vessels, opposite the level or levels to be fused. It is believed to be advantageous to stagger the ports slightly from direct opposition to each other.

The preferred method continues with insertion of retractors through the ports 142, 143. The retractors can be used to sweep the small bowel superiorly out of the pelvis. The sigmoid colon is also pulled out of the pelvis and held laterally with the left fan retractor. For fusion at the L5-S1 junction, the sacral promontory and drop-off can be easily seen at this point. The posterior peritoneum overlying the L5-S1 disc space is then incised longitudinally with endoshears for the desired exposure. Using opposing fan retractors as blunt dissectors, the soft tissue underlying the parietal peritoneum can be swept laterally to bilaterally expose the anterior L5-S1 disc annulus. The sacral artery and vein coursing the disc are individually ligated with hemoclips and transected. A dissector can be used to remove residual soft tissue over the disc. Exposure is maintained with the left fan retractor in place holding the colon out of the way. It has been found that usually the right side does not require retraction, so a suction irrigation catheter can be used through this port.

In one specific procedure for the L4-L5 disc, the posterior peritoneum is incised more proximally about 3 centimeters. Again, the left fan is used to retract the colon laterally and with careful blunt dissection the aorta is exposed anteriorly at the bifurcation. The L4-L5 disc is usually right below this point. Left lateral dissection is carried out over the left common iliac vein and artery, gently retracting these vessels to the right. In order to retract these vessels enough to the right for adequate disc exposure the ascending segmental vein branch must be identified and transected. Once this vessel is cut, the artery and vein can then be bluntly retracted to the right with a fan or loop retractor to expose a significant amount of the L4-L5 disc for fusion.

Once the subject disc is exposed, it can be important to align the abdominal entry operating trocar port site 145 with the disc to be fused so that the operating trocar is parallel with the endplates of the disc in the sagittal plane. The entry point is estimated and a small Steinmann pin can be placed either in the interspace or along the patient and checked with lateral C-arm and adjusted accordingly. A 1.5 to 2.5 centimeter incision can be made for placement of the operating trocar. A blunt introducer is placed in the abdomen and an 18 mm working trocar 147 (FIG. 11) can be placed over it under endoscopic visualization.

In accordance with a further aspect of the present embodiment of the surgical technique, the annulus of the subject disc D is marked for bilateral placement of a pair of fusion devices. For example, as shown in FIG. 11, a working trocar 147 is situated within the working port 145 (see FIG. 10). The bilateral marks can be made with a template 150, as shown in FIG. 11 and in more detail in FIG. 12. Greater detail concerning this template and its method of use can be found in co-pending application Ser. No. 08/427,432, filed on Apr. 24, 1995. The description of this template in this co-pending application is incorporated herein by reference.

Figure 12:
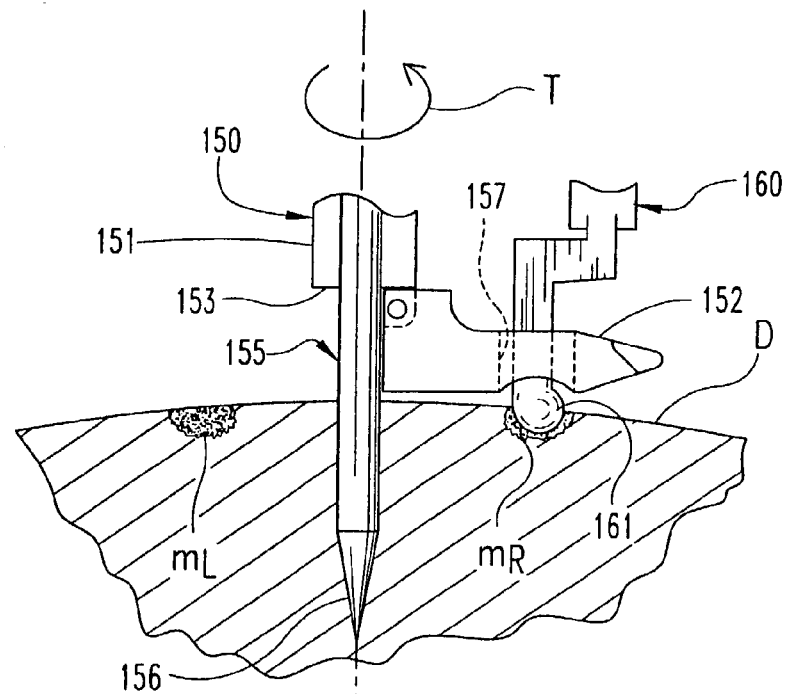
FIG. 12 is an enlarged A-P view of the disc at the spinal segment showing the use of the template represented in FIG. 11 of the invention.

For convenience, a brief description of the template will be made with specific reference to FIG. 12. In particular, the template 150 includes tubular body 151 and an elongated guide foot 152 that is pivotably connected to the end 153 of the tubular body. A guide wire or stylet 155 extends through the tubular body to pivot the foot 152 to the side. The sharp tip 156 of the stylet can then be used to pierce the disc annulus D. Using a mallet, the template can be secured to the center of the disc space by driving the stylet 156 into the disc tangential to the curvature of the annulus and parallel to the endplates. The template can then be slid down the guide wire or stylet until the foot 152 contacts the disc annulus.

The foot includes an opening 157 through which an electrocautery device 160 can extend. The tip 161 of the electrocautery device is guided through the opening 157 in the foot 152 to contact the disc annulus D. When the tip 161 is energized, it leaves a mark MR that is lateral to the center of the subject disc. The template 150 can then be rotated in the direction of the arrow T so that the foot is situated laterally opposite the first mark MR. At that point, the electrocautery device can be used to make a second mark ML providing the bilateral positions for the two fusion devices.

Figures 14, 15:
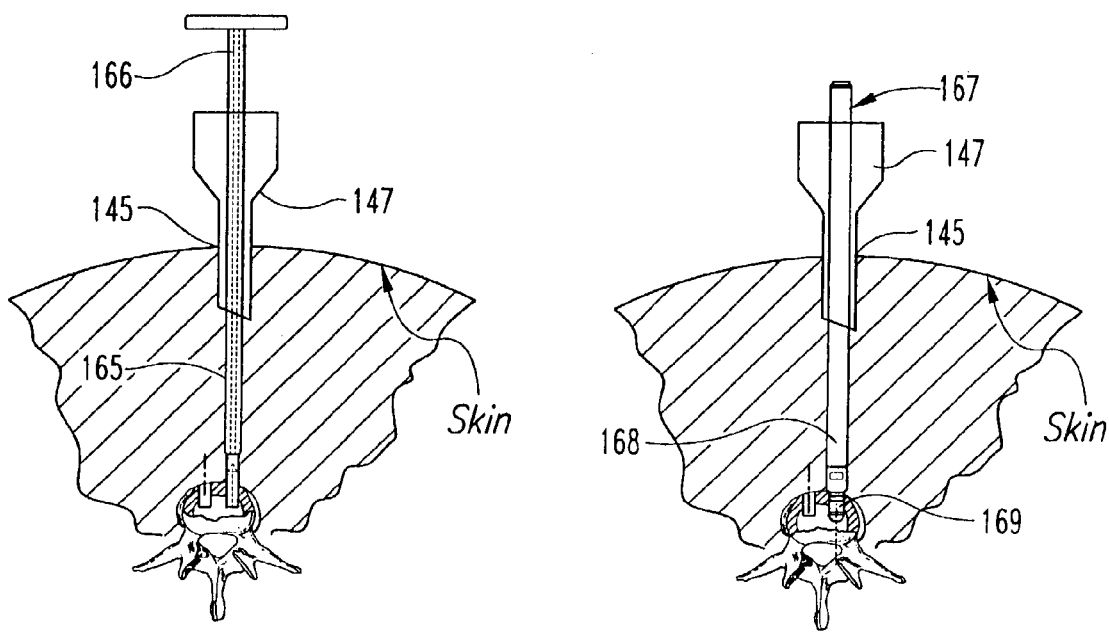
FIG. 14 is an A-P representation of the laparoscopic surgical site depicting a further step of the inventive surgical technique of using a trephine to create a bore at each of the bilateral locations marked in the step shown in FIG. 11.
FIG. 15 is an A-P representation of the laparoscopic surgical site depicting a further step of the inventive surgical technique for inserting a distractor into the prepared site at each of the bilateral locations marked in the step shown in FIG. 11.

Once the bilateral marks MR, ML have been made on the disc annulus, the surgeon has a visual indication as to the proper location for placement of the fusion device. Under direct visualization of the insufflated abdominal region by way of a laparoscope through port 141 (FIG. 10), the surgeon can then direct a T-handle probe 160 through the working port 147 to the either of the cauterization marks MR and ML. The T-handle probe 160 includes a sharp tip 161 that is used to break through the disc annulus. The T-handle allows the surgeon to rotate the probe 160 as necessary to facilitate penetration into the annulus. Once an initial opening has been made in the disc annulus by way of the T-handle probe 160, a T-handle trephine 165 can be used to create pilot holes for subsequent instrumentation. The T-handle trephine 165 can include a series of markings 166 at 5 mm increments to control the depth of insertion of the trephine into the disc space, as shown in FIG. 14. The markings 166 are compared to the working trocar 147 to gauge the depth of the cutting edge of the trephine, and therefore the depth of the prepared bore in the disc space and vertebral endplates. Again, the T-handle of the trephine allows the surgeon to rotate the trephine 165. This procedure is repeated at both of the electrocautery marks ML and MR. At this point, the surgeon has two bilateral holes to use for orientation during the remainder of the procedure. The trephine 165 is also preferably used to core into the disc space to form bilateral bores. A rongeur may be used to clear disc material from each of the bilateral bores in the disc.

In accordance with further steps of the present inventive method, a distractor 167 is advanced through the working trocar 147 as shown in FIG. 15. The distractor has a distractor tip 169 that is selected according to the vertebral level being instrumented. For instance, distractors for a 16 mm size implant can be either 12 mm or 14 mm in width to maintain the disc space at its proper anatomical height. The tip 169 is removably attached to a distractor shaft 168. Preferably, progressively larger distractor tips are sequentially inserted in alternating fashion into each of the bilateral holes in the disc space and annulus until the annulus is taut and the adjacent vertebrae are adequately distracted for restoration of a proper disc space height. In one aspect of the invention, the distractor tips 169, once they are disposed in their bilateral positions, will act as a centering point or alignment guide for use of the instruments throughout the remainder of the procedure. It is therefore important that the distractor tips 169 be properly located, which can be accurately confirmed with fluoroscopy.

Figure 16:
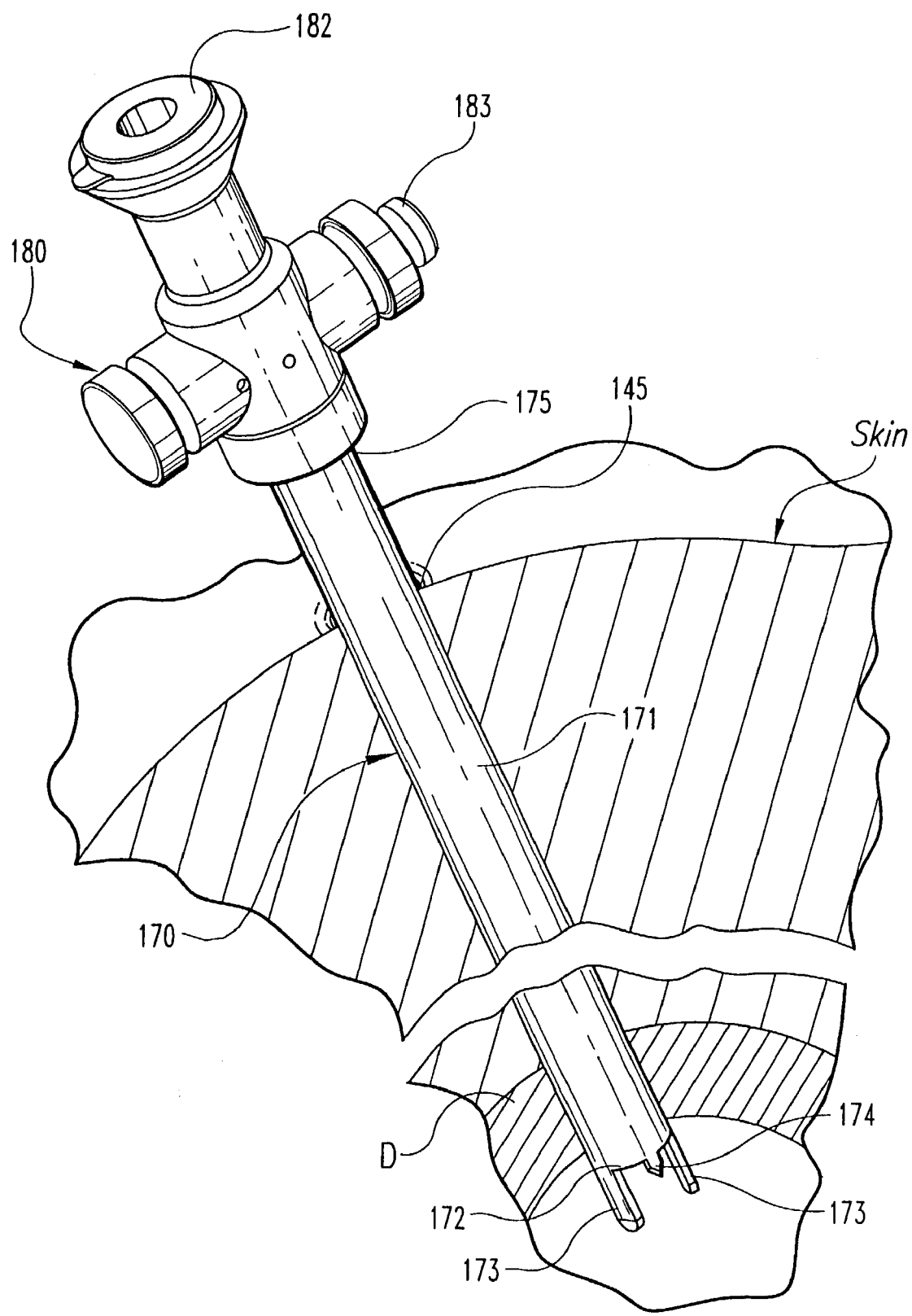
FIG. 16 is a perspective representation of the laparoscope according to the present invention in which the outer sleeve of the laparoscope is engaged within the subject disc space.

Once the bilateral distractor tips have been properly seated, a shaft extension (not shown) can be engaged to distractor shaft 168. At this point, in accordance with the preferred embodiment, the disposable trocar 147 is removed and a laparoscope 170 is introduced through the port 145 in the skin and into the disc space, using the distractor shaft and distractor tip as a positioning guide. In accordance with one embodiment of the present invention, the laparoscope 170 includes an outer sleeve 171 having a first end 172 and a second end 173, as shown in FIG. 16. The second end 173 is engaged to a laparoscopic port 180 which can be of conventional design. In particular, the laparoscopic port 180 can include a bore 184 (FIG. 17(*a*)) extending therethrough and in communication with the interior of the hollow outer sleeve 171. This bore 184 in the laparoscopic port allows introduction of instruments through the port and into the outer sleeve 171. The bore is preferably closed by a number of seals 182, which are configured to accept cylindrical tools and instruments therethrough while maintaining tight sealed engagement about the instrument.

The laparoscopic port 180 also preferably includes a trumpet valve 183, which can be of conventional design. Specifically, the trumpet valve 183 maintains the laparoscopic port 180 in a normally closed position in which its internal bore is closed from communication with the outer sleeve 171. However, once an instrument is introduced into the port 180 through the seals 182, the trumpet valve 183 moves aside to allow passage of the instrument or tool into the sleeve 171.

In a further unique aspect of the invention, the end 172 of the outer sleeve 171 includes a pair of opposite distraction extensions or fingers 173. These distraction fingers 173 are sized according to the height of the particular disc space. Specifically, the fingers 173 are intended to maintain the spacing between the adjacent vertebrae during subsequent steps of the procedure after the distractor tip 169 has been removed. Thus, the width of the fingers 173 can be varied depending upon the particular vertebral level being instrumented. In addition, the distraction fingers 173 can be tapered to conform to a normal angle between adjacent vertebrae at the instrumented level. The position of the fingers 173 is correlated with the position of the distractor tips within the bilateral bores in the disc space by aligning the fingers 173 with the trumpet valve 183 when the port 180 is engaged to the outer sleeve 171. When the laparoscope 170 is inserted, the trumpet valves provide a visual indication of the alignment of the fingers. In other words, when the trumpet valve 183 is lateral to the midline, the fingers 173 are properly oriented between the vertebral endplates.

In one specific embodiment, the outer sleeve 171 can include opposite spikes 174 disposed between the distraction fingers 173. These spikes are preferably configured to penetrate at least partially into the adjacent vertebral bodies, to help maintain the position of the outer sleeve 171 at the surgical site. In some instances, the outer sleeve 171 does not include the teeth 174. For example, where the procedure is to implant a tapered fusion device, the teeth 174 are preferably eliminated and where the device is a uniform cylinder, the teeth can be retained.

Figures 17A, 17B:
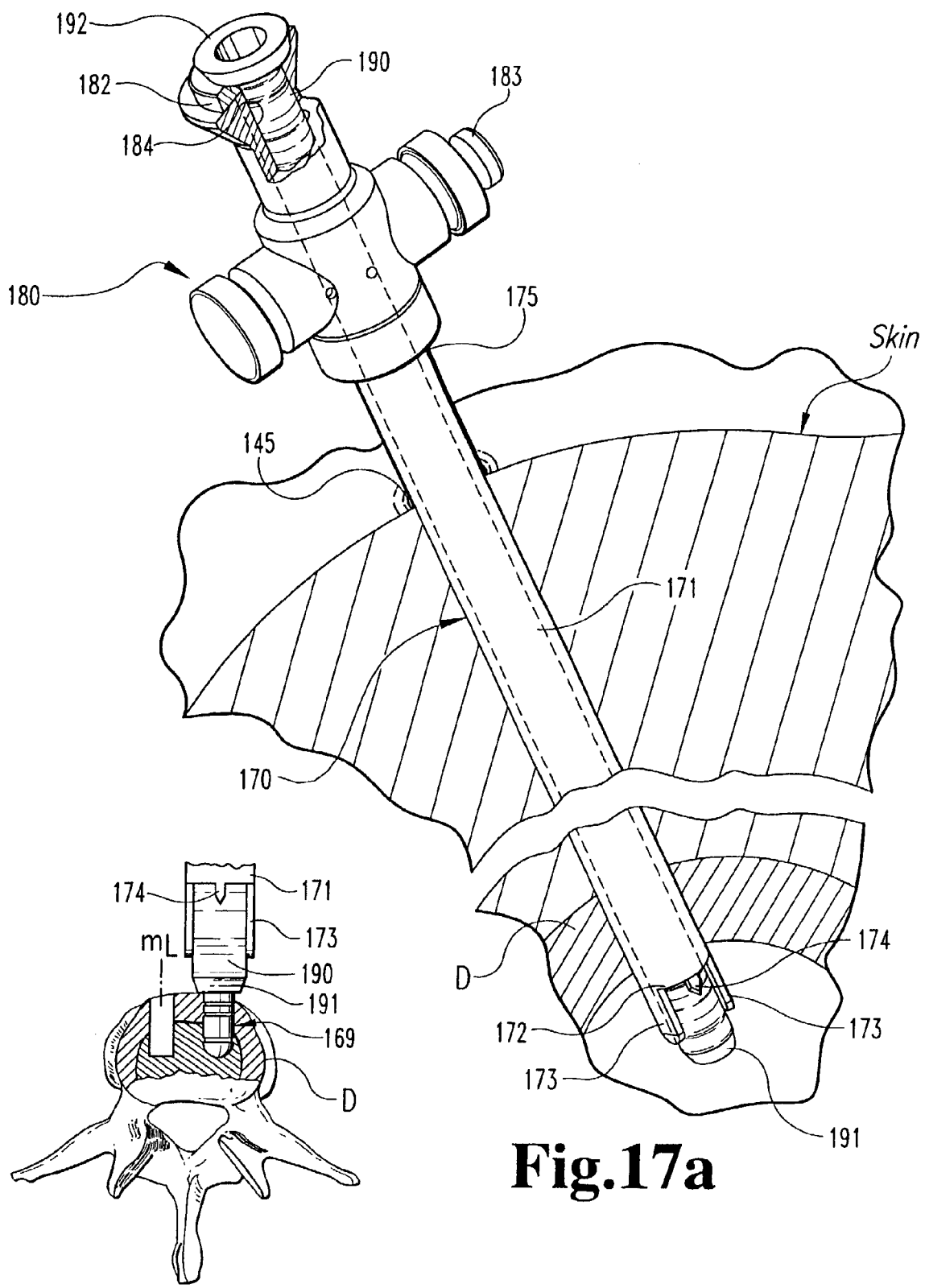
FIG. 17(a) is a perspective representation of the laparoscope of FIG. 16 with a switching sleeve according to one aspect of the invention disposed within the laparoscope.
FIG. 17(b) is an enlarged A-P representation of the laparoscope and switching sleeve of FIG. 17(a) showing the positioning of a distractor tip as depicted in FIG. 15.

In one embodiment of the present surgical method, the laparoscope 170 can be directly inserted over the distractor shaft extension (not shown). However, it is believed that the distraction fingers 173 and the spikes 172 can cause trauma to the skin during entry and to the soft tissue surrounding the surgical site during introduction of the laparoscope 170. Thus, a further feature of the preferred embodiment includes a switching sleeve 190, as shown in FIGS. 17(*a*),(*b*). The switching sleeve 190 has a length sufficient to span the entire length of the laparoscope 170 from the port seals 182 to the end 172 of the outer sleeve 171. In particular, the switching sleeve 190 has a tapered tip 191 configured to extend beyond the end 172 of the outer sleeve 171, and more particularly beyond the ends of the fingers 173. The switching sleeve 190 also includes a flared tip 192 at its opposite end that is enlarged to prevent its passage through the laparoscopic port 180 and particularly the seals 182.

In accordance with a preferred embodiment of the inventive surgical procedure, the switching sleeve 190 is placed inside the laparoscope 170 prior to insertion into the patient. The switching sleeve 190 has an outer diameter nearly equal to the inner diameter of the outer sleeve 171 to slide in close running fit within the laparoscope 170. The laparoscope 170 and switching sleeve 190 can then be slid over the distractor shaft and with a twisting motion pass through the skin and fascia until the outer sleeve contacts the disc annulus. It is important to consider that the opposite fingers 173 on the outer sleeve 171 of the laparoscope must pass through the opening in the disc space and be aligned between the adjacent vertebrae. As the fingers 173 are pushed into the disc space, the switching sleeve 190 will remain outside the disc annulus as its tapered tip 191 contacts the annulus in the region between the distraction fingers 173 (see FIG. 17(*b*)). The outer sleeve 171 of the laparoscope 170 is properly oriented when the fingers 173 are correctly oriented between and contacting the adjacent vertebra endplates. The outer sleeve 171 is then seated by striking a driving cap (not shown) mounted on the laparoscopic port, to thereby drive the fingers 173 fully into the disc space between the vertebral endplates and to drive the spikes 174 into the adjacent vertebrae.

With the laparoscope 170 in place, all of the remaining steps of this inventive technique occur under a relatively protected or sealed environment. Specifically, the outer sleeve 171 of the laparoscope provides a sealed passageway from the bilateral bores at locations MR and ML on the disc to the laparoscopic port 180 outside the patient. The laparoscope 170 can be used as a passageway to provide irrigation and aspiration where necessary, without the risk of fluids leaking into the space adjacent the operative site. Moreover, the sealed working channel to the prepared sites in the disc space prevent leakage of abdominal distension fluids into the working channel and disc space. This latter aspect allows direct vision of the surgical site outside the working channel created by the laparoscope.

With the laparoscope 170 in position, the distractor shaft 168 is removed as well as the distractor tip 169 that is disposed between the adjacent vertebrae. Since the fingers 173 of the laparoscope outer sleeve 171 will maintain the spacing between the adjacent vertebrae, the distractor tip is no longer needed. Preferably, the surgeon will firmly grasp the outer sleeve 171 as the distractor tip is being removed from the disc space to prevent dislodgement of the outer sleeve. In a bilateral procedure, the bilateral bores in the disc each contain a distractor tip. In the preferred method, the right distractor tip is removed first while the distractor tip in the left bore remains in place. Thus, the fingers 173 of the laparoscope engaged within one of the bilateral locations share the distraction load with a distractor tip 169 disposed within the other bilateral location. When the right side in instrumented with a fusion device, as described below, the fingers 173 will be within the left bore in the disc and will share the distraction load with the fusion device.

Figure 18:
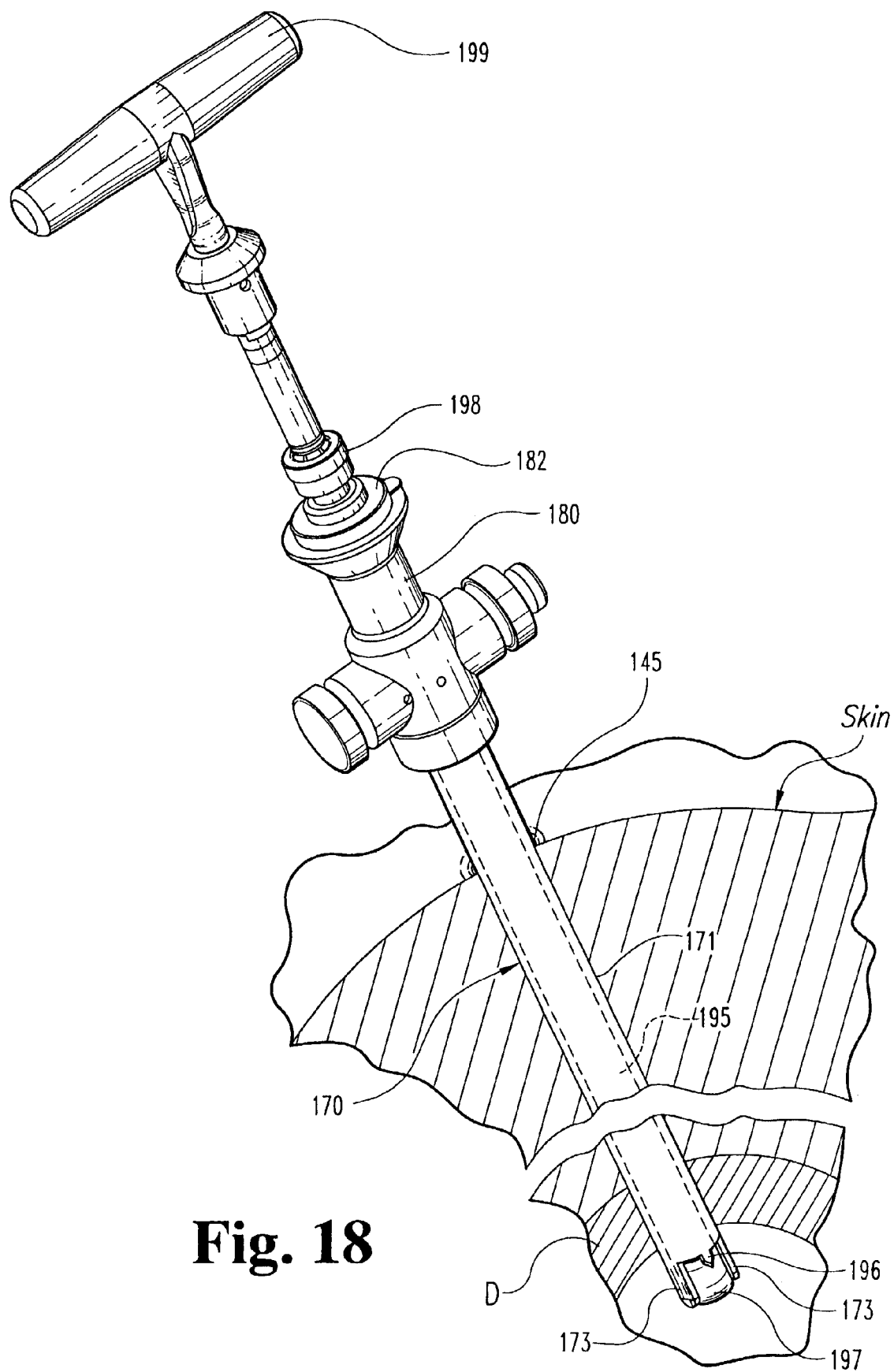
FIG. 18 is a perspective representation of the laparoscope of FIG. 16 with a reamer extending through the laparoscope to prepare the site for receiving a fusion device.

With the distractor tip removed and the disc space supported by the fingers 173, the next step in the inventive method is the preparation of the vertebral end plates and disc to provide a site for insertion of a fusion device. The switching sleeve 190 is first removed and, in accordance with one aspect of the invention, a reaming sleeve 195 is advanced through the laparoscope 170. As shown in FIG. 18, the reaming sleeve 195 includes spikes 196 that are adapted to penetrate the adjacent vertebral bodies to hold the reaming sleeve in place. One object of the reaming sleeve in this embodiment is to help maintain the position of the laparoscope while the disc material and vertebral end plates are being reamed. This object is of particular importance when the laparoscope outer sleeve 171 does not include the teeth 174. In addition, the spikes 196 on the reaming sleeve 195 will prevent the vertebral bodies from being pushed away or distracted while reaming, since the force generated by the reamer can have a tendency to drive the vertebral bodies apart. This force is particularly present when a tapered fusion device is to be implanted, necessitating cutting conical threads into the vertebra.

In accordance with the invention, an adjustable reamer 197 is extended through the reaming sleeve 195. The reamer 197 can be of conventional design with a cutting surface configured to evacuate the disc space and prepare the adjacent vertebral bodies to receive a threaded implant. The reamer 197 includes an adjustable depth stop 198 disposed adjacent the laparoscopic port 180. The depth stop 198 contacts the seals 182 of the port to prevent introduction of the reamer 197 too deeply into the disc space. The depth of reaming necessary, and consequently the position of the depth stop 198, can be determined prior to this reaming step by review of fluoroscopic images.

The reamer 197 is manually operated by way of a T-handle 199 to successively remove disc tissue and bone from the adjacent vertebral bodies to provide a prepared bore for the fusion implant. Preferably, several passes will be made with the reamer, after which the outer sleeve will be examined visually and fluoroscopically to verify that it remains fully seated within the disc space. In addition, the reaming should be observed under C-arm imaging to prevent reaming into the spinal canal. Preferably, the depth stop 198 will be set at an initial drilling depth less than the anticipated full depth for implant insertion. For example, for an L5-S1 fusion, a 20 mm deep reamed bore may be prepared for a 26 mm long implant.

After the disc material and vertebral bodies have been reamed by the reamer 197, one prepared site is available for insertion of the fusion implant at the right location MR. It is then necessary to prepare the other bilateral location previously marked using the template 150 (location ML in FIG. 12). In the next steps of the inventive method, the reamer 197 is withdrawn as well as the reaming sleeve 195. The laparoscope 170 is then unseated in a controlled manner so that the fingers 174 are disengaged from between the vertebrae and withdrawn through the opening of the disc annulus. However, the laparoscope 170, and particularly the outer sleeve 171, is not removed from the skin after unseating from the disc space. Instead, the outer sleeve is reoriented over the second bilateral location ML (see FIG. 12). Preferably, immediately after the outer sleeve 171 is disengaged from the disc annulus, the switching sleeve 190 is extended back through the outer sleeve 171 so that the tapered end 191 of the sleeve extends beyond the fingers 173. The switching sleeve will then protect the soft tissue surrounding the instrumented disc space as the outer sleeve 171 is repositioned over the second bilateral location ML.

With the laparoscope 170 oriented over the second location ML and with the switching sleeve 190 contacting the disc annulus, a distractor tip 169 attached to a distractor shaft 168 is extended through the outer sleeve 171. In the preferred technique, the laparoscope is not yet fully seated at this location ML. The distractor tip 169 is advanced through the bore within the disc and anchored between the adjacent vertebral end plates. The laparoscope 170, and particularly the outer sleeve 171, is reseated within the disc space in the manner described above, namely with the distraction fingers 173 disposed between the vertebral end plates. Once the position of the outer sleeve and fingers 173 is confirmed using fluoroscopy, the remaining steps for preparing the vertebral bodies to receive the fusion implant are repeated at the left location ML.

Figure 19:
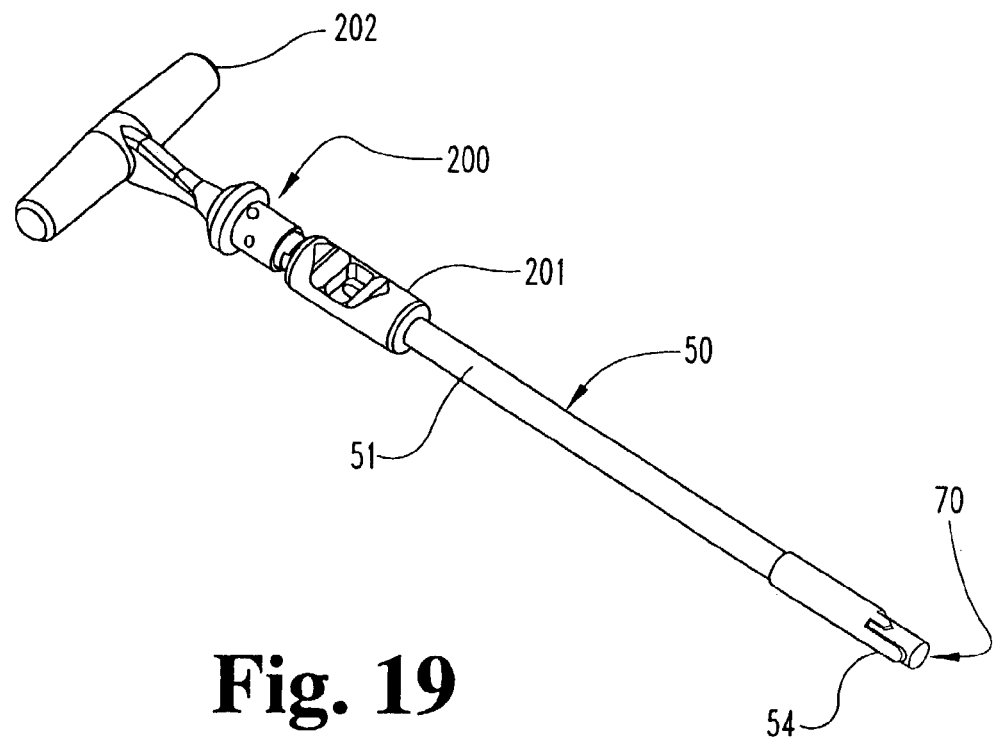
FIG. 19 is is a perspective view of an implant driver of the type shown in FIG. 2 engaged to a fusion device and including a T-handle assembly engaged to the driver.
Figure 20:
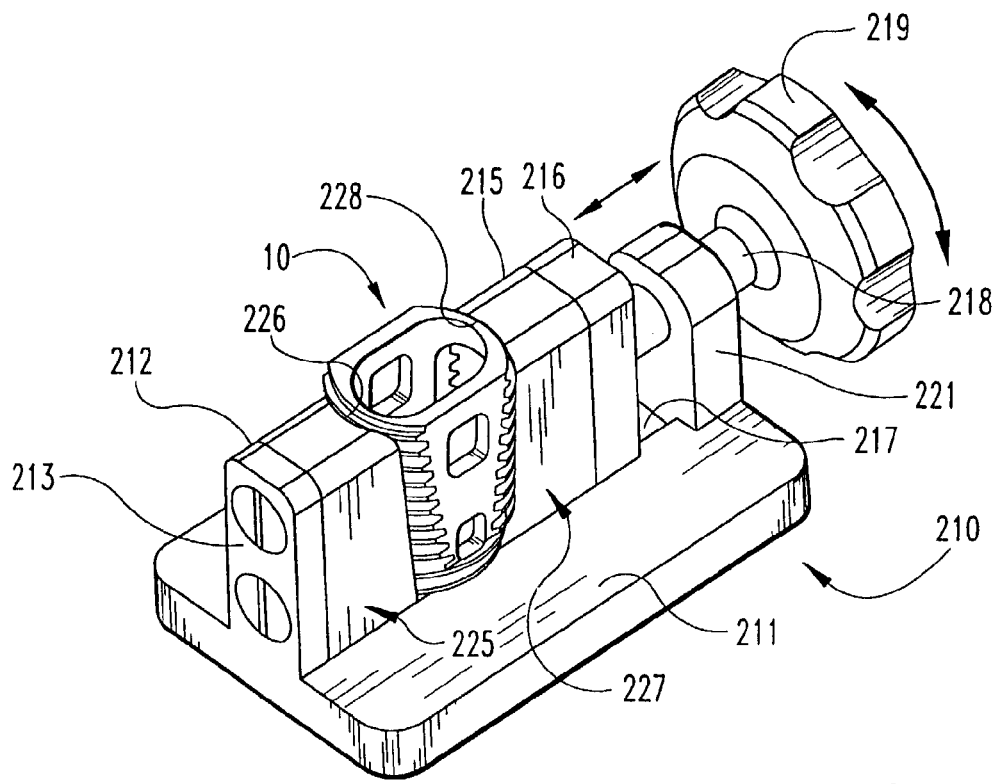
FIG. 20 is a perspective view of an implant holder according to one aspect of the present invention.

Once the second bore in the disc space has been prepared, the following steps of the technique involve insertion of the implant. In accordance with the present invention, the implant can be a fusion cage of the type shown in FIG. 1 which is tapered to restore the normal curvature at the particular vertebral level. In the case of a fusion cage of the type shown in FIG. 1, the implant driver 50 can be used to implant the device 10. The implant driver 50 can be substantially as depicted in FIG. 2 and can engage the implant 10 as shown in FIG. 3. In accordance with the present technique, the implant driver 50 can be engaged by a T-handle assembly 200, as shown in FIG. 19. The T-handle assembly 200 includes a collet 201 which engages the end of the implant driver 50 opposite the gripping tongs 54. The assembly 200 also includes T-handle 202 which is aligned with the gripping tongs 54 so that the surgeon has a visual indication of the orientation of the tongs 54 when the implant driver 50 is extended through the laparoscope 170.

In accordance with the preferred technique, the implant driver 50 carrying the fusion device 10 is inserted through the laparoscopic port 180 and through the outer sleeve 171 until the implant 10 contacts the prepared bore within the disc space. At that point, the implant driver 50 can be rotated using the T-handle 202 to thread the implant into the prepared bore. The implant driver 50 can preferably include a plurality of depth markings on the driver shaft 51 beneath the collet 201 to give the surgeon the visual indication of the depth of insertion of the implant 10 into the prepared bore. Once the implant has been screwed in to its predetermined depth, as indicated by the depth markings on the implant driver shaft 51, insertion of the implant should be halted with the T-handle 202 parallel to the vertebral end plates. With this orientation of the T-handle 202, the tongs 54 of the implant driver 50 will be exposed to the disc space, rather than in contact with the vertebral bone. Consequently, then the long slots 27 (see FIG. 1) of the fusion device 10 will be directly exposed to and in contact with the vertebral bodies.

With a fusion device 10 implanted within the left location ML, the implant driver is removed from the implant and the laparoscope 170 is unseated from the left bilateral location. Again, the laparoscope 170 is not removed from the skin after unseating, but is simply moved to the next bilateral location MR, preferably with the switching sleeve 190 protecting the surrounding tissue from the distraction fingers 173 of the laparoscope. At this location, the same steps are repeated to implant a second fusion device 10 at this right location.

When each of the implant devices 10 is bilaterally implanted within the disc space, the position of the implants should be confirmed. In some instances, it may be necessary to reposition an implant within the disc space, such as by driving it further into the disc space. In this instance, the driving attachment 120 can be engaged to the implant driver 50 and the attachment 120 engaged with the implanted device 10 to permit additional manipulation of the device.

In switching between the left location RL and the right location MR, it is preferred that the implant driver 50 be fully removed from the laparoscope 170 and the switching sleeve 190 extended through the outer sleeve 171. Also, the distractor tip 169 attached to the distractor shaft 168 should then be extended through the switching sleeve 170 and the distractor tip can be used to locate the previous bore at the right location MR. Once the distractor tip 169 is situated within the bore, the outer sleeve 171 can be seated at the right most location in the disc space. With the outer sleeve 171 properly seated, the distractor shaft can be removed to make way for the implant driver 50 carrying a new implant fusion device 10. Of course, the switching sleeve is removed prior to extending the implant and implant driver through the outer sleeve 171.

Once both fusion devices are disposed in their bilateral positions at locations ML and MR, an A-P radiograph can be taken to assure proper placement. In addition, where possible, it is preferred that additional bone graft material is packed around the implants in situ to further facilitate fusion.

As discussed above, the fusion device 10 includes a hollow opening 15 to receive bone growth material. In one specific embodiment, this bone growth material can include autogenous bone harvested from the patient's anterior iliac crest. Autograft bone from other locations, autologous bone, allograft, bone growth substitutes or other bone material capable of promoting or inducing bone ingrowth can be loaded into the implant. In the preferred technique, the interior 15 of each fusion implant 10 is filled prior to insertion of the implant into the disc space.

To facilitate this "pre-loading" of the fusion material, an implant holder 210 is provided in accordance with the invention. This holder 210 includes a base 211 that includes a fixed clamp section 212 and a movable clamp section 215. The fixed clamp section 212 includes a flange 213 projecting from the base 211. The movable clamp section includes an impactor plate 216 that slides within a groove 217 formed in the base 211. The impactor plate 216 is connected by a threaded shaft 218 to a knob 219. The threaded shaft is rotationally supported by an upstanding flange 221 attached to the base 211. The upstanding flange 221 includes a threaded bore (not shown) through which the threaded shaft 218 extends. As the knob 219 is rotated, the shaft rotates within the threaded bore of the flange 221 to move the impactor plate 216 forward toward the fixed clamp half 212.

In accordance with the present embodiment, a pair of blocks 225 and 226 are provided which are disposed adjacent a corresponding one of clamp sections 212 and 215. The blocks 225 and 227 include implant engagement surfaces 226 and 228 which are configured to match the outer shape of the implant at its large slots 27. These blocks, therefore, serve to close off the slots 27 as bone growth material is packed into the opening 15 of the implant 10. In one specific embodiment, the blocks 225 and 227 are formed of plastic to effectively seal the large openings 27 in the sides of the implant 10. Once the bone growth material has been tightly compacted within the implant device 10, the knob 219 can be rotated in the opposite direction to release the movable clamp 216 from the device 10.

Figure 21:
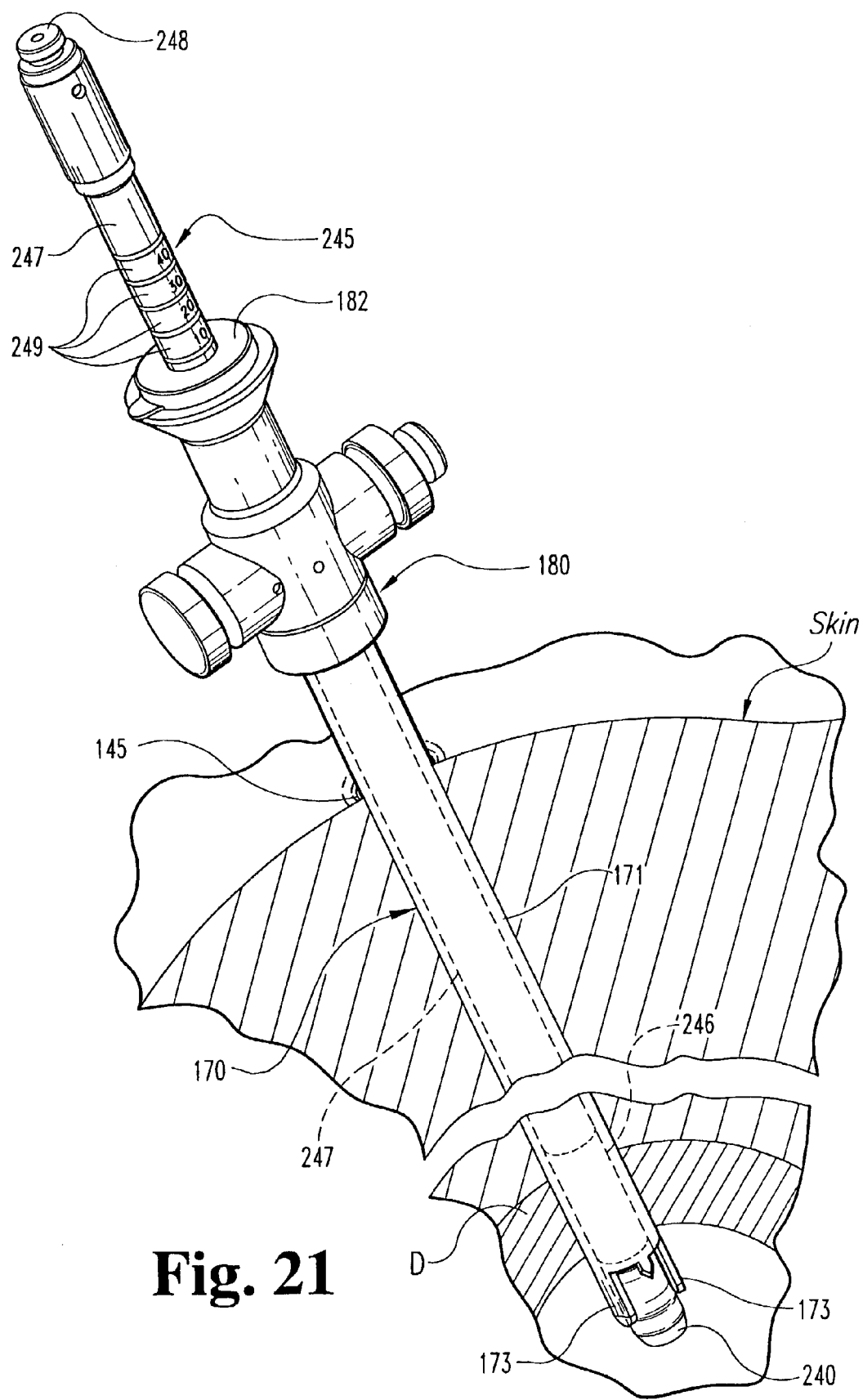
FIG. 21 is a perspective representation of the laparoscope used to implant a bone dowel within the prepared site and including a bone dowel impactor in accordance with one aspect of the present invention.

In accordance with another aspect of the present invention, the laparoscope 170 can be used to implant a bone dowel 240, as depicted in FIG. 21. The bone dowel 240 can be of a variety of configurations, such as an allograft Crock dowel, autograft tricortical or button dowels, manufactured composite dowels or hybrid dowels (e.g., an autogeneuos button combined with al allograft Crock dowel). While it is preferable that the bone dowel 240 be cylindrical, this configuration is not essential to the invention, provided the dowel is configured to pass easily through the outer sleeve 171 of the laparoscope.

In accordance with this embodiment, the disc space and adjacent vertebral bodies are prepared as described above (see, FIGS. 10-18 and accompanying text). In the preferred technique for implanting a bone dowel, the reamer 197 is used to create a partially cylindrical cut in the vertebral endplates to receive a cylindrical dowel. Alternatively, if a non-cylindrical dowel is used, the endplates can be prepared accordingly. It is understood that the dowel will typically have a uniform outer diameter or width corresponding to the disc space height. Unlike the fusion device 10 discussed above the bone dowel is not tapered; however, preparation of the vertebral bodies with the tapered distraction fingers 173 of the outer sleeve 171 providing an appropriate angle will allow the implanted bone dowel to retain this angle.

Once the disc space and vertebral endplates have been prepared to receive the dowel, the bone dowel 240 is dropped into the laparoscope through outer sleeve 171. Due to the precise fit between the bone dowel and the vertebral endplates, resistance will be experienced during insertion of the dowel. An impactor 245 is provided to drive the dowel into its prepared site. The impactor includes an impactor head 246 that is prefereably threaded engaged to an impactor shaft 247. The head and shaft are sized for a close running fit through the outer sleeve 171. Preferably, the impactor head 246 can be provided in several diameters depending upon the size of the bone dowel to be implanted. Also preferably, the impactor shaft 247 will have a smaller diameter so that it can be used with impactor heads and outer sleeves of several diameters.

The impactor shaft 247 includes a driving cap 248 that can be stricken by a hammer or similar tool to drive the bone dowel into the prepared site in a controlled manner. Preferably, the impactor shaft also includes a series of depth markings 249 corresponding to the depth of insertion of the bone dowel 240 into the disc space. The final position of the dowel can be verified later by A-P radiograph. The second bone dowel can be inserted in a similar manner and additional bone graft placed between the bilateral bone dowels.

The present invention involves instruments and surgical techniques usable at any level of the spine. For simplicity, the above discussion has focused on fusion of the L5-S1 disc space. The dimensions of each of the components of the instruments would be sized appropriately for the specific vertebral level being instrumented. For example, the fusion devices 10 may be offered in several sizes, including 12 mm, 14 mm and 16 mm. Based upon the size of the fusion implant, the trephine 165 can be provided in several sizes, such as trephines to form bores having a diameter of 6 mm, 8 mm or 10 mm.

The distractor tips 169 are also sized according to the size of the fusion device to be implanted. Preferably, the distractors are smaller than the fusion device. For example, for a 16 mm fusion device, the distractor tips 169 can be either 12 mm or 14 mm. For a 16 mm fusion device, a 16 mm reaming sleeve is provided to accept a 16 mm reamer to prepare a hole of the same diameter within the disc space and vertebral bodies. Smaller reamers and reaming sleeves would be provided for smaller fusion devices. As previously described, the outer sleeve 171 of the laparoscope 170 is preferably a 2 mm in diameter to readily accept all of the instruments and sleeves passing therethrough during the several steps of the inventive procedure.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for performing a spinal procedure, comprising:
    making an incision in a patient's skin adjacent a vertebral disc space;
    providing a laparoscope having a sleeve with oppositely disposed fingers extending from one end of the sleeve and a laparoscopic port positioned adjacent an opposite end of the sleeve, the fingers configured to maintain distraction of the vertebrae adjacent the vertebral disc space, the laparoscopic port including a number of seals;
    providing an insertion member including a distal tip portion;
    inserting the insertion member into the laparoscopic port and through the number of seals to provide sealing engagement between the insertion member and the sleeve with the distal tip portion extending beyond the distal end of the sleeve;
    advancing the sleeve through the incision with the port positioned outside the patient;
    engaging the distal tip portion of the insertion member with the vertebrae;
    inserting the fingers into the vertebral disc space to define a protected channel between the vertebral disc space and the laparoscopic port;
    inserting a surgical cutting instrument through the seals of the laparoscopic port and through the sleeve; and
    cutting into at least one of the vertebral disc material and one or both of the adjacent vertebrae with the surgical cutting instrument adjacent the vertebral disc space.

2. The method of claim 1, wherein the distal tip portion of the insertion member is tapered.

3. The method of claim 1, wherein distal tip portion of the insertion member extends beyond the fingers of the sleeve during the engaging.

4. The method of claim 1, further comprising:
    providing a removable cylindrical member defining an interior passage;
    inserting the removable cylindrical member into the laparoscopic port and through the number of seals to provide sealing engagement between the removable cylindrical member and the sleeve;
    introducing a surgical instrument through the interior passage of the removable cylindrical member.

5. The method of claim 4, wherein the removable cylindrical member precludes contact between the surgical instrument and the number of seals.

6. The method of claim 1, wherein the number of seals are provided by a seal member including an annular flange portion positioned in abutment against a proximally-facing end surface of the sleeve.

7. The method of claim 1, wherein the cutting comprises at least one of drilling and tapping.

8. The method of claim 1, further comprising delivering an implant through the sleeve and into an opening in the vertebral disc space.

9. A method for performing a spinal procedure, comprising:
providing a laparoscopic vertebral distractor including an elongated member having proximal and distal end portions and defining a longitudinal opening, the distal end portion including two spaced apart arms, the proximal end portion including a laparoscopic port and having a number of seals;
providing a removable sleeve member defining an interior passage;
inserting the spaced apart arms into a vertebral disc space to distract the adjacent vertebrae;
inserting the removable sleeve member into the laparoscopic port and through the number of seals to provide sealing engagement between the removable sleeve member and the elongated member;
introducing a surgical instrument through the interior passage of the removable sleeve member and the opening of the elongated member; and
cutting into at least one of the vertebral disc material and one or both of the adjacent vertebrae with a cutting instrument adjacent the vertebral disc space.

10. The method of claim 9, wherein the removable sleeve member includes an annular flange portion positioned in abutment against a proximally-facing surface of the proximal end portion of the elongated member.

11. The method of claim 10, wherein the removable sleeve member includes an axial sleeve portion extending from the annular flange portion and into the proximal end portion of the elongated member.

12. The method of claim 11, wherein the annular flange portion of the removable sleeve member is positioned external to the proximal end portion of the elongated member.

13. The method of claim 9, wherein the removable sleeve member precludes contact between the surgical instrument and the number of seals.

14. The method of claim 9, wherein the interior passage of the removable sleeve member includes an inner diameter sized in relatively close tolerance with an outer diameter of the surgical instrument to guide the surgical instrument.

15. The method of claim 9, further comprising:
providing an insertion member including a distal tip portion;
inserting the insertion member into the laparoscopic port and through the number of seals to provide sealing engagement between the insertion member and the elongated member with the distal tip portion of the insertion member extending beyond the distal end portion of the elongated member; and
engaging the distal tip portion of the insertion member with the adjacent vertebrae prior to inserting the spaced apart arms of the elongated member into the vertebral disc space.

16. The method of claim 15, wherein the distal tip portion of the insertion member is tapered.

17. The method of claim 9, wherein the cutting comprises at least one of drilling and tapping.

18. The method of claim 9, further comprising delivering an implant through the elongated member and into an opening in the vertebral disc space.

* * * * *